(12) United States Patent
Medina

(10) Patent No.: US 7,322,369 B2
(45) Date of Patent: Jan. 29, 2008

(54) METHODS OF DETACHING MICROORGANISMS FROM, OR OF INHIBITING MICROBIAL ATTACHMENT TO, ANIMAL OR POULTRY CARCASSES OR SEAFOOD OR PARTS THEREOF

(75) Inventor: Marjorie B. Medina, Glenside, PA (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 644 days.

(21) Appl. No.: 10/960,389

(22) Filed: Oct. 6, 2004

(65) Prior Publication Data

US 2005/0224097 A1 Oct. 13, 2005

Related U.S. Application Data

(63) Continuation-in-part of application No. 09/832,211, filed on Apr. 10, 2001, now abandoned.

(60) Provisional application No. 60/196,092, filed on Apr. 11, 2000.

(51) Int. Cl.
*B08B 3/04* (2006.01)

(52) U.S. Cl. ............... 134/25.3; 426/310; 426/321; 426/322; 426/331; 426/332; 426/335; 426/572; 426/652; 514/20; 514/54; 514/57; 514/631; 514/634; 422/28; 422/32; 422/261; 134/36; 134/42; 510/199

(58) Field of Classification Search ........... 426/310, 426/321, 322, 331, 332, 335, 572, 652; 514/20, 514/54, 57, 631, 634; 422/28, 32, 261; 134/25.3, 134/36, 42; 510/199
See application file for complete search history.

(56) References Cited

U.S. PATENT DOCUMENTS

| 2,934,438 | A | * | 4/1960 | Michener et al. ........... 426/326 |
| 2,979,410 | A | * | 4/1961 | Parlour ........................ 426/106 |
| 4,434,181 | A | * | 2/1984 | Marks et al. ............... 514/635 |
| 2002/0009436 | A1 | * | 1/2002 | Doyle et al. ............... 424/94.6 |

* cited by examiner

*Primary Examiner*—Sharidan Carrillo
(74) *Attorney, Agent, or Firm*—John D. Fado; G. Byron Stover

(57) ABSTRACT

Methods of detaching microorganisms (e.g., bacteria) from, or of inhibiting microbial (e.g., bacterial) attachment to, animal or poultry carcasses or seafood or parts thereof, wherein the method involves contacting animal or poultry carcasses or seafood or parts thereof at least once with at least one of the following: (i) a polysulfated polysaccharide, (ii) carboxymethyl cellulose, or (iii) guanidine or arginine, optionally together with sodium chloride and at least one non-ionic surfactant, or (iv) mixtures thereof, in an amount effective to detach microorganisms (e.g., bacteria) from, or inhibit microbial (e.g., bacterial) attachment to, animal or poultry carcasses or seafood or parts thereof.

23 Claims, 16 Drawing Sheets
(9 of 16 Drawing Sheet(s) Filed in Color)

**Detachment for *In Situ* Sampling in Slaughter Plants**

Spray a 300 cm area with Carrageenans,
or Carboxy methyl Cellulose or dextran sulfate Spray same area with arginine
to loosen the bound bacteria Soak sponge with
0.05% Tween 80 (Span 80) and 1% NaCl
or
phosphate buffer with NaCl and Tween 80

Wipe off bacteria from treated surface
with pre-soaked sponge
or
with filter paper (e.g. cellulose or polycarbonate membranes)
or
with vacuum (with filter) to remove bacteria from carcass surface
remove vacuum filter for entrapped bacteria Enrich or Extract bacteria from sponge or filter or membranes Analyze bacteria with
1. Traditional Plate Methods
or
2. Isolate target bacteria
with immunomagnetic beads
or
3. Biosensor screening (BIAcore, etc.)
or
4. Other microbial screening and testing methods

Beef Slaughter Plant Application

Carcass after removal of hide

Post skinning wash

**Inhibitor or Microbial Blocking Agent (*carrageenan or CMC or dextran sulfate*) dispensed in a spray box**

Evisceration

Splitting

**Final wash
(water spray)
Removal of bacterial contamination with
arginine and Tween 80/NaCl or phosphate buffer with Tween/NaCl**

Chill

Fabrication

Trimmings; Primals

**Inhibitor or Microbial Blocking Agent (carrageenan or CMC or dextran sulfate) dispensed as spray or immersion
(Anti-bacterial compound may also be incorporated)**

Packaging

Distribution, retailing

FIG. 1

Poultry (Chicken) Slaughter Plant Application

Kill Room

Scalding/defeathering

Evisceration

Chlorination
(high pressure chlorinated water jets thoroughly clean the entire bird)

Inspection
(for fecal contamination before chilling)

Chilling
(The birds body temp is about 98° F and must be lowered to 40° F or below before processing. Birds are sent to soak in the chiller for 73 minutes. Each chiller holds 20,000 gals. of chlorinated water.)

Inhibitor or Microbial Blocking Agent (carrageenan or CMC or dextran sulfate) dispensed in a spray box Grading
Birds are rehung in shackles to be graded.

Packaging of Whole Birds
or
Cut-up

2nd Inhibitor or MBA (carrageenan or CMC or dextran sulfate) application to cut-ups
(anti-bacterial agent such as Cetyl Pyridium Chloride may be added)
[MBA= Microbial Blocking Agent; CMC= carboxy methyl cellulose]

Boning and trimming

Packaging of cut-up parts

FIG. 2

Swine Slaughter Plant Application in Clean Room

Shaving

Carcass Washing

Head Removal, Brisket sawing, Debunging

Carcass Opening

Evisceration

Carcass Splitting

Trimming

Stamping

Final Carcass Washing
(spraying with room temp. water)

Inhibitor or Microbial Blocking Agent (carrageenan or CMC or dextran sulfate) dispensed in a spray box
(also prevents dehydration)

Chilling
(dry air blast at 2 degrees, overnight)

Cutting

Inhibitor or MBA (carrageenan or CMC or dextran sulfate) application
(anti-bacterial agent such as Cetyl Pyridium Chloride may be added)
[MBA= Microbial Blocking Agent; CMC= carboxy methyl cellulose]

Packaging or Processing

FIG. 3

Detachment for Sampling
[Laboratory Analysis]

Coat tissues with Inhibitor or Microbial Blocking Agent
(Carragenan, CMC or dextran sulfate)

Detach bacteria
Guanidine-HCl, pH 4.8
or
Phosphate buffer-NaCl-Tween 80

Enrich bacterial growth

Analyze bacteria using

1. Traditional Plate Method
or
2. Isolate target bacteria
immunomagnetic beads
or
imuno-affinity silica gel
or
3. Biosensor screening (BIAcore, etc.)
or
4. Other microbial screening and testing methods

FIG. 4

Detachment for *In Situ* Sampling in Slaughter Plants

Spray a 300 cm area with Carrageenans,
or Carboxy methyl Cellulose or dextran sulfate Spray same area with arginine
to loosen the bound bacteria Soak sponge with
0.05% Tween 80 (Span 80) and 1% NaCl
or
phosphate buffer with NaCl and Tween 80

Wipe off bacteria from treated surface
with pre-soaked sponge
or
with filter paper (e.g. cellulose or polycarbonate membranes)
or
with vacuum (with filter) to remove bacteria from carcass surface
remove vacuum filter for entrapped bacteria Enrich or Extract bacteria from sponge or filter or membranes Analyze bacteria with
1. Traditional Plate Methods
or
2. Isolate target bacteria
with immunomagnetic beads
or
3. Biosensor screening (BIAcore, etc.)
or
4. Other microbial screening and testing methods

FIG. 5

Kappa Carrageenan
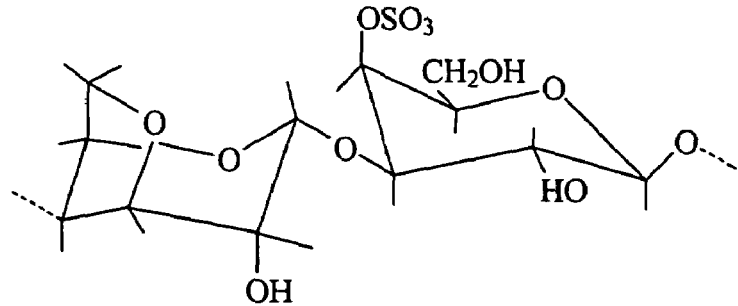
3,6-anhydro-D-galactose D-galactose-4-sulphate
Iota Carrageenan
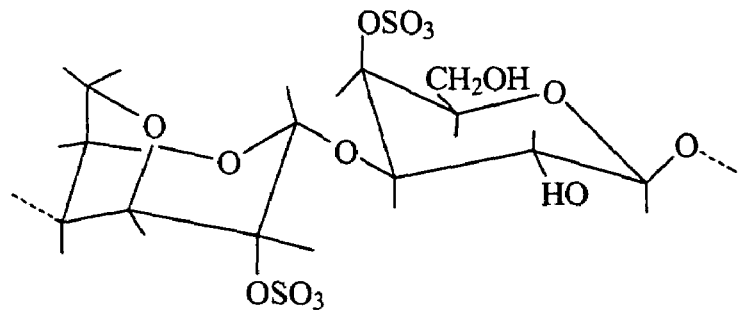
3,6-anhydro-D-galactose-2-Sulphate D-galactose-4-sulphate
Lambda Carrageenan
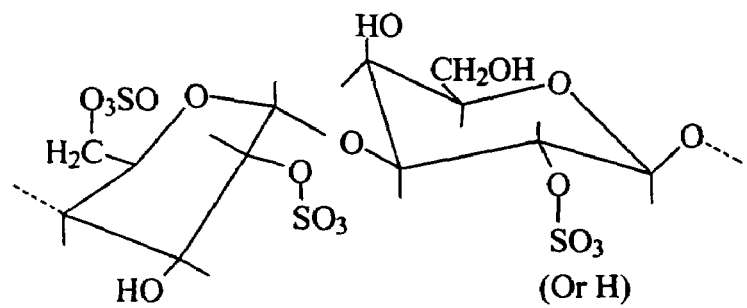
D-galactose-2,6-disulphate D-galactose-2-sulphate
FIG. 6B

US 7,322,369 B2

METHODS OF DETACHING MICROORGANISMS FROM, OR OF INHIBITING MICROBIAL ATTACHMENT TO, ANIMAL OR POULTRY CARCASSES OR SEAFOOD OR PARTS THEREOF

REFERENCE TO RELATED APPLICATION

This application claims the benefit of U.S. Provisional Application No. 60/196,092, filed 11 Apr. 2000, and U.S. patent application Ser. No. 09/832,211, filed on 10 Apr. 2001, now abandoned and which are incorporated herein by reference in their entirety.

BACKGROUND OF THE INVENTION

The present invention relates to methods of detaching microorganisms (e.g., bacteria) from, or of inhibiting microbial attachment to, animal or poultry carcasses or seafood or parts thereof, wherein the method involves contacting animal or poultry carcasses or seafood or parts thereof at least once with at least one of the following: (i) a polysulfated polysaccharide, or (ii) carboxymethyl cellulose, or (iii) guanidine or arginine, optionally together with sodium chloride and at least one non-ionic surfactant, or (iv) mixtures thereof, in an amount effective to detach microorganisms (e.g., bacteria) from, or inhibit microbial (e.g., bacterial) attachment to, animal or poultry carcasses or seafood or parts thereof.

Food borne disease in the U.S. is estimated to occur between 6.5 to 33 million cases per year (Council for Agricultural Science and Technology (CAST), 1994, *Food borne Pathogens: Risks and Consequences*, Task Force Report No. 122). Bean et al. (Center for Disease Control (CDC) (1996), Surveillance for Foodborne-Disease Outbreaks-United States, 1988-1992, Center for Disease Control (CDC), Morbidity and Mortality Weekly Report, 45: 1-65) also reported that bacterial pathogens caused 79% of outbreaks and 90% of cases when the etiology was determined in food borne disease outbreaks in the U.S. from 1988-1992. *E. coli* O157:H7 outbreaks have caused several fatalities, particularly in children. Recently, Mead et al (Food-related illness and death in the United States, Emerg. Infect. Dis., 5: 607-625 (1999)) estimated that in the U.S. there are about 1.3 million cases of illness due to non-typhoidal *salmonella* (9.7% of total food borne pathogen diseases); 15,600 cases of hospitalization (25% of food borne pathogens); and 553 deaths (30.6% of food borne pathogens); these cases are 9.7%, 25% and 30.6% of the total food borne illnesses, hospitalizations and deaths, respectively. The estimates for *E. coli* O157:H7 illness, hospitalization and deaths and 62,458, 1,843 and 52 cases; their respective percent of the total food borne illnesses, hospitalizations and deaths are 0.5%, 3% and 2.9%, respectively. Productivity losses and medical costs were estimated to be in the range of $6.5 to $34.5 billion per year (CAST, 1994). Recent recalls of contaminated beef resulted in millions of dollars in losses for the food industry. Therefore, any new approach to reducing or eliminating pathogen contamination in foods would decrease food borne illness and medical costs and provide savings to the food industry and American taxpayers.

SUMMARY OF THE INVENTION

A method of detaching microorganisms (e.g., bacteria) from, or of inhibiting microbial attachment to, animal or poultry carcasses or seafood or parts thereof, wherein the method involves contacting animal or poultry carcasses or seafood or parts thereof at least once with at least one of the following: (i) a polysulfated polysaccharide, or (ii) carboxymethyl cellulose, or (iii) guanidine or arginine, optionally together with sodium chloride and at least one non-ionic surfactant, or (iv) mixtures thereof, in an amount effective to detach microorganisms (e.g., bacteria) from, or inhibit microbial attachment to, animal or poultry carcasses or seafood or parts thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows Beef Slaughter Plant Application.

FIG. 2 shows Poultry (Chicken) Slaughter Plant Application.

FIG. 3 shows Swine Slaughter Plant Application in Clean Room.

FIG. 4 shows Detachment for Sampling for Laboratory Analysis.

FIG. 5 shows Detachment for In Situ Sampling in Slaughter Plants.

FIG. 6A shows a structure of heparin sulfate and FIG. 6B shows structures of carrageenans.

DETAILED DESCRIPTION OF THE INVENTION

Figure 6A:
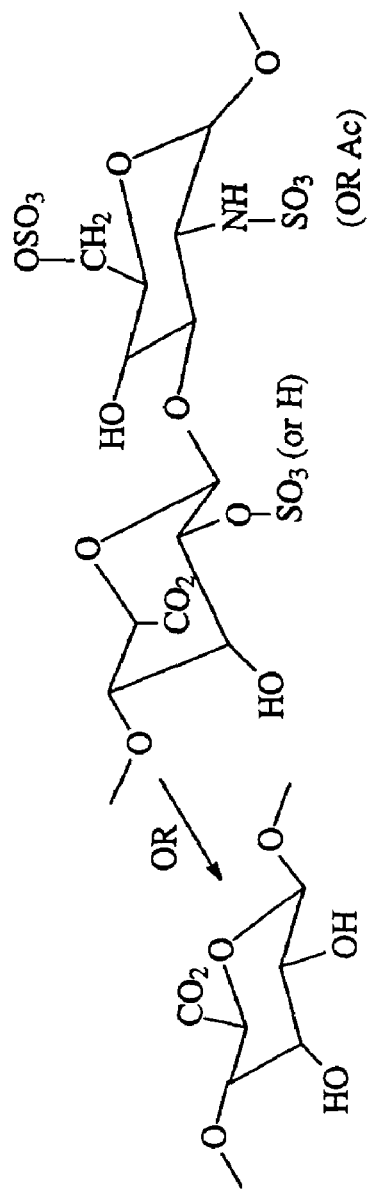

One aspect of the present invention involves a method of detaching microorganisms (e.g., bacteria) from, or of inhibiting (blocking) microbial attachment to, animal or poultry carcasses or seafood or parts thereof. The method involves contacting animal or poultry carcasses or seafood or parts thereof at least once with at least one of the following: (i) a polysulfated polysaccharide (e.g., carrageenan, dextran sulfate), or (ii) carboxymethyl cellulose, or (iii) guanidine or arginine, optionally together with a non-ionic surfactant (e.g., a TWEEN surfactant (sorbitan esters) such as polyoxyethylenesorbitan monolaurate (TWEEN-20 or TWEEN-21) polyoxyethylenesorbitan monopalmitate (TWEEN-40), polyoxyethylenesorbitan monostearate (TWEEN-60 or TWEEN-61), polyoxyethylenesorbitan tristearate (TWEEN-65), polyoxyethylenesorbitan monooleate (TWEEN-80 or TWEEN-81), polyoxyethylenesorbitan trioleate (TWEEN-85), preferably TWEEN-20 and/or TWEEN-80, or a SPAN surfactant such as sorbitan monolaurate (SPAN-20), sorbitan monopalmitate (SPAN-40), sorbitan monostearate (SPAN-60), sorbitan tristearate (SPAN-65), sorbitan monooleate (SPAN-80), sorbitan trioleate (SPAN-85), preferably SPAN-20 and/or SPAN-80) and sodium chloride, or (iv) mixtures thereof, in an amount effective to detach microorganisms (e.g., bacteria) from, or inhibit microbial attachment to, animal or poultry carcasses or seafood or parts thereof; these compounds may be dissolved or suspended in phosphate buffer. This method may be also used in detecting and quantifying microorganisms (e.g., bacteria) on carcasses or parts thereof where the microorganisms must first be detached from the carcasses or parts thereof. As used herein, TWEEN includes all Tweens such as TWEEN-20, TWEEN-21, TWEEN-40, TWEEN-60, TWEEN-61, TWEEN-65, TWEEN-80, TWEEN-81 and the like. SPAN include all Spans, such as SPAN-20, SPAN-40, SPAN-65, SPAN-80, SPAN-85 and the like.

The term "animal" herein includes cattle, pigs, sheep, goats, and other mammals whose meat may be used as food. The term "poultry" herein includes chickens, turkeys, ducks, quail, and geese. The term "seafood" means any fish or shellfish from the sea used for food; see also Code of Federal Regulation; Title 21, Part 161—Fish and Shellfish. The term "parts thereof" means any part of the carcass which is less than the whole carcass, the part may be cut or removed from the whole carcass; the term "parts thereof" also means any part of seafood which is less than the whole seafood, the part may be cut or removed from the whole seafood.

The term "contacting" herein includes spraying, immersing, dipping, submerging, washing, soaking, and other methods (excluding injecting) of applying (i) a polysulfated polysaccharide, (ii) carboxymethyl cellulose, (iii) guanidine or arginine, optionally with sodium chloride and at least one non-ionic surfactant, (iv) or mixtures thereof to the carcasses or parts thereof. The contacting may be during processing or storage. The contacting time that is effective to fully or partially detach microorganisms (e.g., bacteria) from, or fully or partially inhibit microbial (e.g., bacterial) attachment to, animal or poultry carcasses or seafood or parts thereof is easily determined by one skilled in the art (as shown in the examples below). Generally, polysulfated polysaccharides and carboxymethyl cellulose require 2-24 hours at 4° C. Generally, guanidine or arginine require a minimum of 30 minutes.

The method of the present invention may be used at any stage in the processing of animal or poultry carcasses or seafood or parts thereof; in addition, the method may be used at different temperatures utilized at different stages in the processing plant. The amount of (i) polysulfated polysaccharides, (ii) carboxymethyl cellulose, (iii) guanidine or arginine, optionally with sodium chloride and at least one non-ionic surfactant, (iv) or mixtures thereof, that is effective to fully or partially detach microorganisms (e.g., bacteria) from, or fully or partially inhibit microbial (e.g., bacterial) attachment to, animal or poultry carcasses or seafood or parts thereof is easily determined by one skilled in the art (as shown in the examples below). Generally, 0.05-2% (preferably 0.1-0.5%) (w/v) polysulfated polysaccharides (e.g., carrageenans), 0.1-0.5% (w/v) carboxymethyl cellulose, 0.1-2M (preferably 0.5-1.0 M) guanidine or arginine, 0.01-25% (preferably 0.05-1%)(w/v) non-ionic surfactant (e.g., TWEEN-80), and 0.5-3% (preferably 0.85-2) (w/v) sodium chloride may be utilized. These compounds may be dissolved or suspended in 0.05 mM-0.5 M phosphate buffer (sodium or potassium phosphate buffer as a substitute for water).

The animal or poultry carcasses or seafood or parts thereof may be first contacted with a polysulfated polysaccharide or carboxymethyl cellulose and then contacted a second time (1) with a polysulfated polysaccharide or carboxymethyl cellulose or (2) with guanidine or arginine (optionally together with sodium chloride and at least one non-ionic surfactant). The animal or poultry carcasses or seafood or parts thereof may be washed before or after being contacted with the compounds.

Carcass decontamination as spray or immersion bath: The food and animal industry needs a processing method to eliminate or reduce pathogen contamination of foods of animal and poultry and seafood origin. Polysulfated polysaccharides or carboxy-methyl cellulose may inhibit attachment of pathogens from animal and poultry and seafood tissues. In combination with guanidine, arginine and/or salt and at least one non-ionic surfactant, the microorganisms (e.g., bacteria) may be detached from collagen surfaces such as connective tissue, muscle surfaces, fascia, adipose tissues, etc. Polysulfated polysaccharides or carboxymethyl cellulose, in combination with other chemicals, may be used as ingredients in carcass sprays or immersion baths prior to or after chilling of eviscerated slaughtered food animals and poultry and seafood. When combined with bactericidal agents, for example cetylpyyridium chloride, it may also be used to decontaminate cut parts prior to packaging. Treatment of carcasses and parts thereof with the polysaccharides (carrageenans or carboxy methyl cellulose) may also prevent dehydration of the animal and poultry and seafood parts, thus prolonging their quality and providing economic savings (through prevention of water loss in the chilling process) to the industry.

For example, in beef slaughter, the polysulfated polysaccharides or carboxymethyl cellulose may be dispensed by spraying the carcasses after the post-skinning wash and before evisceration. After splitting of the carcass, microbial (e.g., bacterial) contamination may be removed with the final wash containing arginine, phosphate buffer and NaCl/non-ionic surfactant followed by hot water spray. Polysulfated polysaccharide or carboxymethyl cellulose may be applied the second time to cut up parts prior to packaging and distribution (FIG. 1).

For example, in poultry processing, the polysulfated polysaccharides or carboxymethyl cellulose may be dispensed through spraying or immersion in a bath to coat the poultry carcasses after the chilling process. With cut up poultry carcasses, the pieces may be coated by the polysulfated polysaccharide or carboxymethyl cellulose prior to packaging (FIG. 2).

For example, in pork processing, the carcass may be sprayed with polysulfated polysaccharides or carboxymethyl cellulose prior to chilling (air blast at 2° C.). The coating of the carcass with polysulfated polysaccharides also prevents dehydration of the carcass, thus preserving its quality and providing economic savings to the industry caused by the drying effects of the air blast. The cut pieces of pork carcasses may also be coated by polysulfated polysaccharides or carboxymethyl cellulose prior to packaging. Bactericidal agents (e.g., cetylpyyridium chloride) may also be incorporated with the polysulfated polysaccharides or carboxymethyl cellulose (FIG. 3).

In cases where the carcasses have been contaminated, a 2-step processing may be used to detach the microorganisms (e.g., bacteria). First the carcasses may be sprayed or rinsed with polysulfated polysaccharides or carboxymethyl cellulose to destabilize the microorganisms (e.g., bacteria) and this may be followed by spraying with arginine or phosphate buffer and NaCl/non-ionic surfactant to remove the destabilized microorganisms (e.g., bacteria).

The present invention also includes a method of quantifying microorganisms (e.g., bacteria) on carcasses or parts thereof. To enhance detachment of microorganisms (e.g., bacteria) for sampling: Treatment of animal and poultry carcass or seafood with polysulfated polysaccharides or carboxymethyl cellulose followed by guanidine or arginine or phosphate buffer and NaCl/non-ionic surfactant may enhance detachment of microorganisms for sampling and analytical purposes. Guanidine-HCl is more effective than arginine for detachment, but the former is not a food additive and may be toxic, though it can be used for analytical (e.g., detection or quantitation) purposes. At pH 4.8, live bacteria may be recovered with guanidine-HCl. At pH 2.5, guanidine-HCl is bactericidal. Therefore, its use may be limited in the laboratory (FIG. 4). For "in situ" sampling in the slaughter plants, arginine, or phosphate buffer and TWEEN-80/NaCl may be used in place of guanidine (FIG. 5).

Carrageenan and related compounds (polyanionic polysaccharides) are natural substances and are "generally regarded as safe" (GRAS). These compounds are already used in the food industry for thickening, gelling, stabilizing, water holding property, etc. These compounds are produced worldwide and are inexpensive. Such compounds have not been used for pathogen control in the food industry. The price is $3 to $6 per pound depending on the purity. However, various grades of preparation may have varying effects. The use of carrageenans for pathogen control would be less than 1% as an ingredient for carcass wash water treatment. Carrageenans are compatible with chilled carcasses or hot water sprays. The value of commercial slaughter is $51 billion for animal packing and $28 billion for poultry slaughter and processing, thus the additional cost for use of these compounds would be minimal.

Carrageenans are polysulfated polysaccharides with polymers of repeating D-galactopyranose disaccharides (Glicksman, M., 1983, *Food Hydrocolloids*, Vol 2: 73-113, CRC press, Inc. Boca Raton, Fla.). They are extracted from marine red algae (seaweeds) and used as food additives which are classified as "generally regarded as safe" (GRAS) by the Food and Drug Administration. Heparin sulfate is a polymer of repeating disaccharides of glucoronate and N-acetylglucosamine. These compounds were used to study inhibition of bacterial attachment to beef fascia, connective tissues and poultry skin and in the design of methods to control contamination of carcass surfaces with pathogens. FIGS. 6A and B show the structures of heparin sulfate and the sulfated polygalactans (carrageenans). Heparin, heparin sulfate and dextran sulfate are also examples of polysulfated polysaccharides; heparin and heparin sulfate would generally not be used for food purposes.

Carrageenans are defined by the Food and Drug Administration according to their sources and usage and applications (CFR Title 21). Carrageenans are refined hydrocolloid extracted from the families of Gigartinaceae and Solieriacea of the class Rodophyceae (red seaweed); *Chondrus crispus, Chondrus ocelalatus, Euchema cottonii, Euchema spinosum, Gigartina acicularis, Gigartina pistillata, Gigartina radula* and *Gigartina stellata*. The food additive contains sulfated polysaccharide with dominant hexose of galactose and anhydrogalactose. Carrageenans contain sulfates in a range of 20-40% dry weight. Salts of carrageenans include ammonium, calcium, potassium or sodium salts. Carrageenans are used as food additives (e.g., emulsifier, stabilizer or thickener in foods). Polysorbate 80 (TWEEN-80) is used with carrageenan production to facilitate separation of sheeted carrageenan salts of carrageenan from drying rolls. Furcellarans are also polysulfated hydrocolloid from a subtype of Rodophyceae (red seaweed) which contains 8-19% sulfates, dry weight. Other sources of carrageenans are *Gloiopeltis, Iridaea, Furcellaria fastigiata* (Belitz, H.-D., and Grosch, W. (1986), Carbohydrates IN: Food Chemistry, Springer Verlag, New York, N.Y., pp. 201-256), *Hypnea musciformis, Gigartina skottsbergii* (Rees, D. A., (1963), The carrageenan system of polysaccharides, part I the relation between the κ- and λ-components, London J. Chem. Soc., Part II: 1821-1832; Cerezo, (1967), London J. Chem. Soc. (C), 992). The structures, chemistry, functions, applications and food additive uses of carrageenans and polysulfated polygalactans are described by Picullell (Picullell, L. (1995), Gelling Carrageenan, IN: Food Polysaccharides and their applications, (A. M. Stephen, Editor), Marcel Dekker, Inc., pp. 205-244; Belitz, H.-D., and Grosch, W. (1986), Carbohydrates IN Food Chemistry, Springer Verlag, New York, N.Y., pp. 201-256), *Hypnea musciformis, Gigartina skottsbergii* (Rees, D. A., (1963), The carrageenan system of polysaccharides, part I the relation between the κ- and λ-components, London J. Chem. Soc., Part II: 1821-1832; Glicksman, M. (1983), *Food Hydrocolloids*, Vol 2: 73-113, CRC press, Inc., Boca Raton Fla.; Rees, D. A. (1961), Estimation of the relative amounts of isomeric sulphate esters in some sulfated polysaccharides, London J. Chem. Soc., Part IV: 5168-5171; Rees, D. A. (1963), The carrageenan system of polysaccharides, part I the relation between the κ- and λ-components, London J. Chem. Soc., Part II: 1821-1832; Guthrie, R. D., et al. (1968), Carbohydrate Sulphates, IN: Carbohydrate Chemistry, The Chemical Society Burlington House, London, pp. 254-269; Kroschwitz, J. E, et al., Eds. (1994), Encyclopedia of Gum Technology, Volume 12, John Wiley and Sons, New York, N.Y.; Dea, I. C. M. (1982), Polysaccharide conformation in solutions and gels, IN: Food Carbohydrates (D. R. Lineback and G. E. Inglett, Editors), Avi Publishing Co., Westport Conn., pp. 420-457).

The polysulfated and polyanionic polysaccharides (such as carrageenans, dextran sulfate, heparin sulfate, carboxymethylsaccharides, alginates) are useful as Microbial Blocking Agents (MBAs) and Surface Rinse Materials (SRMs) for any food product susceptible to microbiological contamination. Representative products include processed or unprocessed animal and poultry products and Ready to Eat (RTE) foods for human consumption or as part of animal feeds, seafood or aquaculture, and in processed and unprocessed seafood products. The polysulfated and polyanionic polysaccharides are particularly useful in treating whole carcasses or parts thereof, ground meat including red meats, pork, and poultry products to block microbial attachments and detach pathogens from these products.

The polysulfated and polyanionic polysaccharides are effective against microorganisms including bacteria, viruses, protozoa and parasites, these materials are specially useful as intervention agents to prevent contamination and proliferation of human food-borne pathogens and food spoilage microorganisms. Examples of microorganisms that can be detached from animal or poultry carcasses or seafood or parts thereof, or whose attachment to animal or poultry carcasses or seafood or parts thereof may be inhibited, generally include the following: Enteric gram-negative pathogens of *Escherichia coli* (enteropathogenic, enterohemolytic, and enterotoxigenic *E. coli*, especially *E. coli* O17:H7), *Salmonella* species (*S. typhmurium, S. enteredities, S. dublin, S. hartford, S. panama*, etc., especially *S. typhimurium*), *Yersinia* species (*Y. enterocolitica*), *Campylobacter* species (*C. jejuni, C. colerasuis*), *Shigella* species (*S. dysenteriae*), *Aeromonas* species (*A. hydrophila*), *Vibrio* species (*V. parahemolyticus, V. chlorera*); Gram-positive pathogens such as *Staphylococcus* species (*S. aureus, S. epidermidis*), *Listeria* species (*L. monocytogenes*); *Helicobacter* species (*H. pylori*), *Bacillus* species (*B. subtilis, B. cereus*); viruses such as Hepatitis (A), Norwalk and Norwalk-like viruses, Human immunodeficiency virus (HIV), Herpes virus (H. simplex); parasites such as *Chlamydia* species, *Sarcina* species; Protozoa and fungi and yeasts such as Giardia, Cryptosporidum, Entamoeba (*E. histolyca*), Candida (*C. albicans*), Trichomonas (*T. vaginalis*); spoilage microorganisms such as *Pseudomonas* spp., *Bronchothrix thermosphacta, Acinetobacter* spp., *Aerobacter* spp., *Enterobacter* spp., *Moraxella* spp., *Lactobacillus* spp, *Flavobacterium* spp.

The polysulfated and polyanionic polysaccharides are applied at any time during slaughter operations and in the processing of the meat, poultry and seafood products. For example, in the meat slaughter operation after removal of cow hide and prior to evisceration and/or after sanitizing treatment, after cutting and in treatment of the comminuted meat products during and after grinding, and in processing into various products. The MBAs and SRMs can also be applied in the poultry slaughter operation, during carcass washing, preferentially after sanitizing, after cutting up of the poultry into parts and during grinding of the muscle parts into comminuted raw (uncooked), cooked and Ready to Eat products. The inventive material can also be used to treat molluscs or shellfish prior to cultivation and in a depuration process to purge pathogenic microorganisms from the seafood product.

The following examples are intended only to further illustrate the invention and are not intended to limit the scope of the invention as defined by the claims.

Experimental Procedures and Results:

Biosensor Studies: A novel approach to study bacterial attachment to animal carcass was designed. The studies led to a development of a biosensor method to study binding of extracellular matrix components to the surface of immobilized bacteria. This novel approach utilized immobilized whole *E. coli* cells. This approach allowed the study of the binding of the lipopolysaccharides and other bacterial surface epitopes without altering their chemical structure. Conditions for immobilization and determination of the bacterial cell surface binding properties were initially assessed with anti-*E. coli* 0157:H7 antibody (Medina et al. (1997), Real-time analysis of antibody binding interactions with immobilized *E. coli* O157:H7, Biotechnology Techniques, Vol. 11 (3): 173-176). The bacterial surface was bound with an antibody produced against a heat-killed bacteria. A model system was developed to study attachment or binding of biochemically unaltered extracellular matrix and carcass macromolecules such as collagen I, laminin, fibronectin and glycoaminoglycosides (Medina, M. B., and P. F. Fratamico (1998), Binding interactions of collagen I, laminin and fibronectin with immobilized *E. coli* 0157:H7 using surface plasmon resonance biosensor, Biotechnology Techniques, Vol. 12 (3): 235). Using the binding of collagen-laminin to *E. coli* surface, this system was then utilized for binding studies of the carcass macromolecules and inhibition of their binding to *E. coli* surfaces by carrageenans, polysulfates and other polyanionic gums (Medina, M. B. (1998), Mechanisms of Enterogenic Bacterial Attachment and Inhibition of *E. coli* O157:H7 Binding to Extracellular Matrix Proteins and Tissues, Presented at the 1998 Joint PAASE, DOST and UP Conference, Manila Philippines (Abstract); Medina, M. B. (1998), Biosensor Studies of Collagen and Laminin Binding with Immobilized *Escherichia coli* O157:H7 and Inhibition with Naturally Occurring Food Additives, Presented in SPIE's International Symposium on Industrial and Environmental Monitors and Biosensors: Pathogen Detection and Remediation for Safe Eating (EB20), Nov. 1-6, 1998, Boston, Mass. (Abstract); Medina, M. B. (1998), Biosensor Studies of Collagen and Laminin Binding with Immobilized *Escherichia coli* O157:H7 and Inhibition with Naturally Occurring Food Additives, Proceedings of SPIE—The International Society for Optical Engineering, pp. 97-104). The binding interactions of polysulfated polysaccharides such as heparan sulfate and iota, lambda and kappa carrageenans were determined with the extracellular matrix proteins (ECM) and the immobilized *E. coli* O157:H7 cells. The carrageenans inhibited and mediated the detachment of the macromolecules from the bacterial surface. Without being bound by theory, these properties are presumably due to the biochemical interactions with collagen and laminin, thus blocking the binding of adhesins from the bacterial surface. This biosensor technique was used to assess the binding properties of collagen, laminin, fibronectin, actin and myosin with the surfaces of immobilized *Salmonella typhimurium* ATCC 14028 and DT104 H3380.

Carrageenans and heparan sulfates are polysulfated polysaccharides (FIG. 1). Carrageenans are polymers of repeating D-galactopyranose disaccharides (Glicksman, M. (1983), *Food Hydrocolloids*, Vol 2: 73-113, CRC press, Inc., Boca Raton, Fla.). They are extracted from marine red algae (seaweeds) and used as food additives which are classified as "generally regarded as safe" (GRAS) by the Food and Drug Administration. Heparan sulfate is a polymer of repeating disaccharides of glucoronate and N-acetylglucosamine. The carrageenans inhibited and detached the macromolecules from the bacterial surface. Without being bound by theory, these properties are presumably due to biochemical interactions with collagen and laminin, thus blocking the binding of adhesins from the bacterial surface. Optical and electron microscopy studies also show the pattern of inhibition. It has been demonstrated that the *E. coli* O157:H7 bound and attached to collagen as shown in biosensor and electron microscopy studies (Medina 1998).

Collagen is the major component (40%) of the connective tissues. Results from the scanning electron microscopy studies illustrated the abundance of collagen strands in the fascia and connective tissues (Medina et al. (1999), Scanning Electron Microscopy Studies on Attachment of *Escherichia Coli* O157:H7 to Bovine Tissues, Presented at 1999 IFT Annual Meeting, Chicago, Ill., July 24-28; Poster at Gordon Research Conference on Molecular Mechanisms of Microbial Adhesions (Aug. 1-6, 1999) and at the 18th Annual Meeting of the Philippine-American Academy of Science and Engineering, Jekyll Is., Ga., Aug. 13-15, 1999). This study also showed the attachment of bacterial cells to single strands of collagen fibril. The fat globules were also wrapped with collagen fibrils where the bacteria attached. The number of bacterial cells were more abundant in crevices of the inoculated tissues. Carrageenans and other structurally related food additives prevented binding of *E. coli* O157:H7 to collagen and reduced attachment of *E. coli* O157:H7 to bovine connective tissues. The binding and dissociation properties of these carrageenans were shown with collagen. Without being bound by theory, the proposed mechanism for its inhibition is perhaps due to competitive binding of these food additives with LPS and other bacterial surface epitopes. If a carcass surface is treated first with these compounds, bacterial LPS and other surface epitopes can not bind to the carcass. The initial phases of bacterial attachment result from the interactions of collagen, LPS and O antigen. However, these food additives showed weak bactericidal effect shown by plating in TSP or BHI media or Buttterfield's buffer. The inhibition results from these biosensor studies are shown in Tables 1, 2a, 2b, and 3; carrageenans were from Ingredient Solutions (formerly Shembreg USA), Searsport, Me.

TABLE 1

Biosensor studies showing % Inhibition of collagen-laminin binding to the E. coli surface by polysulfated polysaccharides (100 μg/ml)

| Inhibitors | Trial 1 % Inhibition | Trial 2 % Inhibition | Trial 3 % Inhibition | Trial 4 % Inhibition | Mean % Inhibition | Sample Standard Deviation |
|---|---|---|---|---|---|---|
| Heparin-SO$_4$ | 40 | 41 | 35 | 41 | 39 | 2.87 |
| iota-Carrageenan | 64 | 81 | 91 | 79 | 79 | 11.15 |
| λ-Carrageenan | 99 | 97 | 99 | 97 | 98 | 1.15 |
| κ-Carrageenan 104 | 73 | 67 | 73 | 69 | 71 | 3 |
| κ-Carrageenan 888 | 96 | 88 | 96 | 88 | 92 | 4.6 |

TABLE 2a

Typical binding interactions of food additives with collagen and *Salmonella typhimurium* Sensor Surface.

| Sample Injected | Bound RU | % Bound to ST sensor | % Inhibition |
|---|---|---|---|
| Collagen | 1850 | 100 | — |
| +PBS | 0.2 | 0 | — |
| +Kappa-888 | 11 | 0.5 | 99.5 |
| +Kappa-104 | 133 | 6 | 94 |
| +Kappa-C8 | 180 | 8 | 92 |
| +Kappa-C1 | 129 | 6 | 94 |
| +Alginate, Na | 1074 | 50 | 50 |
| +Pectin, LM | 1766 | 82 | 18 |
| +Dextran SO$_4$ | 12.1 | 0.6 | 99.4 |

RU = response units or signals from collagen bound to the bacterial sensor. Polysaccharide: Collagen ratio = 1:2 (50 μg/ml polysaccharides in 100 μg/ml collagen). % Bound is binding RU of collagen/polysaccharide mixtures/binding RU of collagen. % inhibition is 100 − % bound × 100.

TABLE 2b

% Inhibition of collagen I binding to immobilized *Salmonellla typhimurium* by kappa-carrageenans and other polysaccharides.

| Poly-saccharides | Collagen: Polysaccharides (50:100 μg/ml) | Collagen: Polysaccharides (100:50 μg/ml) | Collagen: Polysaccharides (50:10 μg/ml) |
|---|---|---|---|
| Kappa-8 | 100 | 99.5 | 67 |
| Kappa-1 | 100 | 95.9 | 61 |
| Kappa-C8 | 99.6 | 91.7 | 52 |
| Kappa-C1 | 100 | 94 | 63 |
| Alginate, Na | 79 | 50 | 17 |
| Pectin, LM | 0 | 18 | 8 |
| Dextran SO$_4$ | 98 | 99.4 | 97 |

Kappa-1, -8, -C8, -C1 are various preparations of food grade kappa-carrageenan. The ratio of collagen and polysaccharides tested were 1:2, 2:1 and 5:1. % inhibition = 100 − % bound × 100 where % Bound is binding RU of collagen/polysaccharide mixtures/binding RU of collagen

TABLE 3

Biosensor studies showing % Inhibition of collagen binding to bacterial surfaces by various gums and hydrocolloids

| | Symbols (not standard) | E. coli O157:H7 | Salmonella typhimurium | Salmonella typhimurium DT104 |
|---|---|---|---|---|
| Dextran Sulfate | DS | 100 | 99.4 | not tested |
| Alginic Acid, Na form | SA | 50 | 50 | not tested |
| Low Methoxy Pectin | PLM | 5 | 18 | not tested |
| Agar (non-sulfated polygalactan) | NSA | 54 | 74 | 62 |
| Gum arabic | GA | 5 | 30 | 42 |
| Keltone (sodium alginate) | KSA | 36 | 77 | 70 |
| Tragacanth 1 | TG1 | 0 | 0 | 2 |
| Tragacanth 2 | TG2 | 16 | 12 | 8 |
| Locust bean gum | LBG | 13 | — | 11 |
| Xanthan | XG | 29 | 17 | 20 |
| Gum karaya | GK | 18 | 18 | 11 |
| Polygalacturonic acid | PG | 35 | — | 37 |
| Carboxymethyl cellulose | CMC | 84 | 89 | 85 |
| Heparan sulfate (bovine intestinal mucosa) | INH | 40 | | |
| Heparan sulfate (bovine kidney) | INH | 38 | | |

In Table 3 are more data on the ability of other polysaccharides and other compounds to inhibit or detach the pathogens from collagen. The results obtained by the BIAcore studies have unexpectedly been shown to be also effective in tissues. The BIAcore studies provide a model system to rapidly assess the effectiveness of food additives and other compounds for inhibition and detachment of bound pathogens. The results are reported as relative % inhibition of collagen binding to bacterial surface compared to equal concentration of kappa carrageenan are indicated below. See also Palumbo, S. A., and M. B. Medina (1998), "Quantitative determination of pathogen reduction during animal slaughter and food processing to provide the scientific basis of HACCP and risk assessment", 1998 Progress Report on Food Safety Research Conducted by ARS, ARS-USDA, Beltsville, Md., December 1998, pp. 90-100; Luchansky, J. B., S. Palumbo, and M. Medina (1999), "Quantitative determination of pathogen reduction during slaughter and food processing to provide the scientific basis of HACCP and Risk Assessment", 1999 Progress Report on Food Safety Research Conducted by ARS, ARS-USDA, Beltsville, Md., December 1999, pp. 91-94.

The inhibitory responses of various preparations and sources of kappa-carrageenan showed 89-99.9% inhibition of collagen binding to the *E. coli* O157:H7 surface. In contrast, the sodium alginate (SA) and low methoxy pectin (PLM) inhibited only 43 and 5% respectively. In this study, the affinity constants of collagen to *E. coli* and *Salmonella* binding in 12 trials (each) ranged from $10^7$ to $10^8$ ($M^{-1}$) with a mean of $3.0 \times 10^8$ ($M^{-1}$) for *E. coli* and $2.75 \times 10^7$ ($M^{-1}$) for *Salmonella*. These compounds (polysaccharides) had no direct binding to the bacterial surface but bound to an immobilized calf skin collagen. The dissociation constants of bacteria and collagen binding ranged from $10^{-8}$ to $10^{-9}$ ($K_D$Mole) while kappa-carrageenans and collagen binding had typically $10^{-10}$ ($K_D$Mole). These kinetics indicate that the carrageenans compete for the same binding sites on the collagen surface and their binding is also much tighter or stronger than the bacteria-collagen binding. These polysaccharides could compete with the polysaccharides, such as LPS, on the bacterial surface epitopes.

Tissue In Vitro Studies:
  Detachment Protocol:
Cut Samples (beef fascia or chicken skin, 4×4 cm);
Decontaminate with 5% $H_2O_2$;
Inoculate with *E. coli* to beef fascia or *Salmonella* to chicken skin 3 h at 4° C.;
Wash off excess unbound bacteria with 3× sterile $H_2O$;
Plate and count 3rd wash;
Detach bacteria with 0.2% INL or 0.3% INK;
Plate and count and treat with 0.75M guanidine HCl pH 4.8 (2×) for final detachment.
  Inhibition Protocol:
Cut Samples (veal fascia or chicken skin, 4×4 cm);
Decontaminate with 5% $H_2O_2$;
Coat tissues with inhibitor (0.2% L-carrageenan or 0.3% K-carrageenan) overnight at 4° C.;
Squeeze out excess inhibitor;
Inoculate with *E. coli* to beef fascia or *Salmonella* to chicken skin for 3 h at 4° C.;
Wash off excess unbound bacteria 3× with sterile $H_2O$;
Plate/count 3rd wash;
Detach bacteria with 0.2% L-carrageenan or 0.3% K-carrageenan);
Plate and count and further wash with 0.75M guanidine HCl pH 4.8 (2×);
Plate and count.

Veal Fascia Tissue Analysis:

Results on Inhibition of *E. coli* O157:H7 attachment by carrageenan and detachment with guanidine HCl

| Sample test | Detachment | Inoculum/ extract | Wash 2 CFU/ml | INL Detached | Guan. |
|---|---|---|---|---|---|
| 1. PBS (Blank) | PBS-Guan. | 0 | 0 | 0 | 0, 0 |
| 2. *E. coli* | PBS-Guan. | $5.8 \times 10^2$ | 0 | $4.2 \times 10^2$ | 0, 0 |
| 3. *E. coli* | INL-Guan. | $6.2 \times 10^2$ | 18.5 | 73 | 0, 0 |
| 4. *E. coli* | INL-Guan. | $1 \times 10^3$ | 0 | 0 | 0, 0 |
| 5. INL; *E. coli* | INL-Guan. | $7.5 \times 10^2$ | 0 | 0 | 0, 0 |

PBS = Phosphate buffer;
PBS-Guan = Phosphate buffer followed by guanidine wash;
INL = λ-carrageenan;
INL-Guan. = λ-carrageenan followed by guanidine wash;
Samples were inoculated with $10^{-5}$*E. coli* 0157:H7 ($9 \times 10^3$ cfu/ml).
Two log CFU were washed off.
One log CFU remained in tissue (see inoculum/extract).
Some bacteria were washed off in the first wash.
Sample 3 had remaining bacteria in Wash 2.
Attached *E. coli* was removed (detached) in samples 2 and 3 after INL treatment.
No *E. coli* was recovered in sample #5 pretreated with INL and washed with PBS and guanidine.
No *E. coli* was recovered in guanidine HCl wash.

Chicken Skin Tissue Analysis

Results on Inhibition/detachment of *Salmonella Typhimurium* ATCC 14028 (ST) Inoculated on Chicken Skins.

| Sample Test | Detachment Cpd | Detached CFU | Guanidine, pH 2.5 |
|---|---|---|---|
| 1. ST | PBS | 26, 52 | 0, 3 |
| 2. ST | PBS | 16, 27 | 0, 1 |
| 3. ST | INL-Guan. | 21, 8 | 10, 10 |
| 4. ST | INL-Guan. | 12, 10 | 0, 25 |
| 5. INL; ST | INL-Guan. | 27, 20 | 4, 0 |
| 6. INK; ST | INL-Guan. | 9, 8 | 4, 0 |

PBS = Phosphate buffer;
PBS-Guan = Phosphate buffer followed by guanidine wash;
INL = λ-carrageenan;
INL-Guan. = λ-carrageenan followed by guanidine wash;
INK = κ-carrageenan 888.
Samples were inoculated with $10^5$ *Salmonella typhimurium* (18 hr culture). Each reported CFU is an average of two plate counts and represents actual counts.
More CFUs were detached by INL-guanidine detachment than PBS alone. (Second guanidine detachment had 0 bacteria.)
Samples #5 and #6 were pretreated with INL and INK respectively. INK inhibited attachment of ST to poultry skin. INK (0.3%) is more effective than INL (0.2%).
Inhibitors directly bind to collagen and prevent bacterial binding. Same CFUs in PBS and INL treatment. Actual detachment is facilitated by guanidine -HCl.

Use of Guanidine, creatine and arginine: Guanidine is a strong cytotoxic compound and can not be used in large quantities in food plants or slaughter operations. It is a very effective detachment agent to detach the bacteria bound to collagen. However, its use may be limited in the laboratory for analysis of food tissues. Therefore, a substitute for guanidine for detachment of pathogens from food carcasses was investigated. Guanidine is structurally related to creatine and arginine with a guanidyl moeity in their molecules. However, with the biosensor studies, creatine proved ineffective. It has been shown that creatine hydrolyzes upon dissolution in water or buffer converting it to creatinine (methylglycocyamidine), a cyclic product and an end product of creatine metabolism. In contrast, 0.5M arginine was equally good or better than 1 M guanidine-HCl to detach the bacteria from the collagen complex. The biosensor studies showed that its effectiveness to detach bacteria bound to collagen is enhanced with the use of TWEEN-80 and NaCl. TWEEN-20 and NaCl only partially detached the bound bacteria from collagen. Arginine is an essential amino acid for children but not for adults. It is non-essential for adults because it can be derived from proteins in the diet. It is also inexpensive and can be obtained in bulk. Phosphoric acid (0.1M), HCl (0.1M) and citric acid (0.5M) had no effect in the detachment studies.

Data on Detachment of *E. coli* O157:H7 from Inoculated Bovine Tissues

Experimental Procedure:

1. Beef bottom round was thinly sliced (approx. 2 mm thick) and cut up into 5×5 cm.
2. Veal fascia and connective tissues were separated from veal breast and cut up into 5×5 cm.
3. *E. coli* O157:H7 was grown in 25 ml BHI broth at 37° C., overnight (16 hrs).
4. The bacteria was diluted up to $10^{-3}$ (approx. $10^6$ CFU) for inoculation.
5. The bovine tissues were decontaminated with 20 ml 5% hydrogen peroxide for 30 min.
6. The excess peroxide was squeezed off and the tissues were transferred to stomacher bags containing to 50 ml sterile water.
7. The excess water was squeezed off from the tissues and transferred to stomacher bags containing 20 ml of peptone buffer.
8. *E. coli* inoculum (0.1 ml) diluted to $10^{-3}$ was transferred to tissue samples.
9. The *E. coli* were allowed to attach to the tissues for 30 min at room temperature.
10. The bacterial population in tissue inoculum was plated and counted.
11. The tissues were transferred to stomacher bags containing 50 ml sterile water to rinse off excess bacteria.
12. The bacteria was detached using the detachment procedure outlined in the following tables.
13. The detachment procedures used 25 ml of the combination of water, polysaccharides (INK=k-carrageenan, CMC=carboxymethylcellulose, DS=dextran sulfate), 0.05% TWEEN-80 (same as SPAN-80) mixed with 0.125N (0.9%) sodium chloride and 0.75M (15%) arginine (food grade substitute of guanidine)

Number of Samples Analyzed: Each treatment had duplicate tissue samples. The culture for inoculation and the unattached bacteria in inoculated samples were plated in three dilutions on duplicate BHI agar.

Detachment Procedures: The bacteria was detached by the combination of water, polysaccharides, arginine, NaCl/non-ionic surfactant were plated in 0 to 2 dilutions on duplicate BHI agar.

Sample: Beef Bottom Round

Trail I Inoculum: $1.42 \times 10^6$ CFU, No. of analysis (n)=6; Trial II Inoculum: $2.47 \times 10^6$ CFU, n=6;

Trial III Inoculum: $2.07 \times 10^6$, n=6

| Detachment Procedure I | Trial I CFU[1] | Trial II CFU[2] | Trial III CFU[3] |
|---|---|---|---|
| Water-TWEEN-80/NaCl | $2.73 \times 10^2$ | $3.12 \times 10^2$ | $4.11 \times 10^2$ |
| INK-TWEEN-80/NaCl | $2.80 \times 10^2$ | $3.38 \times 10^2$ | $1.76 \times 10^2$ |
| CMC-TWEEN-80/NaCl | $6.41 \times 10^2$ | $5.36 \times 10^2$ | $6.94 \times 10^2$ |
| DS- TWEEN-80/NaCl | $1.04 \times 10^3$ | $3.11 \times 10^2$ | $1.47 \times 10^2$ |
| TWEEN-80/NaCl (2×) | | $2.66 \times 10^2$ | $6.70 \times 10^2$ |

[1]Highest detachment with DS followed by TWEEN/NaCl (DS-TWEEN-80/NaCl), then by CMC followed by TWEEN/NaCl > INK > water + TWEEN/NaCl

[2]Highest detachment with CMC followed by TWEEN/NaCl (CMC + TWEEN/NaCl).

[3]Highest EC detachment with CMC + TWEEN/NaCl and 2× TWEEN/NaCl. Lower EC recovery in INK and DS + TWEEN/NaCl.

CMC and TWEEN/NaCl show the highest detachment but the difference is less than one log.

Sample: Beef Bottom Round Inoculum: $5.28 \times 10^5$ CFU, n=6

| Detachment Procedure II | Trial I CFU |
|---|---|
| Water-TWEEN-80/NaCl | $5.18 \times 10^2$ |
| INK-TWEEN-80/NaCl | $4.11 \times 10^2$ |
| CMC-TWEEN-80/NaCl | $7.85 \times 10^2$ |
| DS-TWEEN-80/NaCl | $3.73 \times 10^2$ |
| TWEEN-80/NaCl (3×) | $1.10 \times 10^3$ |

Detachment is highest with 3 × TWEEN/NaCl, then by CMC + 2 × TWEEN/NaCl > H₂O > INK > DS + TWEEN/NaCl Sample: Beef Fascia Connective Tissues Trial I Inoculum: $7.73 \times 10^6$ CFU, n = 6;
Trial II Inoculum: $1.23 \times 10^6$ CFU, n = 6

| Detachment Procedure III | Trial I CFU[1] | Trial II CFU[2] |
|---|---|---|
| Water-TWEEN-80/NaCl (2×) | $1.14 \times 10^3$ | $1.33 \times 10^3$ |
| INK-TWEEN-80/NaCl (2×) | $1.23 \times 10^3$ | $1.21 \times 10^3$ |
| CMC-TWEEN-80/NaCl (2×) | $1.14 \times 10^3$ | $1.41 \times 10^3$ |
| DS-TWEEN-80/NaCl (2×) | $1.03 \times 10^3$ | $4.62 \times 10^2$ |
| TWEEN-80/NaCl (3×) | $1.43 \times 10^3$ | $8.95 \times 10^3$ |

[1]Three rinses with TWEEN/NaCl detached the highest number of CFUs, then INK + 2 × TWEEN/NaCl; CMC and H20 + 2 × TWEEN washes; and DS + 2 ×/NaCl washes.

[2]Three rinses with TWEEN/NaCl detached the highest number of CFUs, then CMC + 2 × TWEEN/NaCl > H20 + 2 × TWEEN washes; and INK + 2 ×TWEEN/NaCl washes. Again, the differences among the detachment procedures were less than one log CFU.

This detachment procedure (III) seem to have the highest detached bacteria which were in the $10^3$ levels.

Sample: Beef Fascia Connective Tissue

| Inoculum: $6.54 \times 10^5$ CFU, n = 6 | | | |
|---|---|---|---|
| Detachment Procedure IV | CFU | Detachment Procedure V | CFU[2] |
| Water-TWEEN-80/NaCl-Arginine | $3.32 \times 10^2$ | Water-TWEEN-80/NaCl-Arginine-TWEEN/NaCl | $3.32 \times 10^2$ |
| INK-TWEEN-80/NaCl-Arginine | $8.75 \times 10^2$ | INK-TWEEN-80/NaCl-Arginine-TWEEN/NaCl | $9.13 \times 10^2$ |
| CMC-TWEEN-80/NaCl-Arginine | $4.30 \times 10^2$ | CMC-TWEEN-80/NaCl-Arginine-TWEEN/NaCl | $4.61 \times 10^2$ |
| DS-TWEEN-80/NaCl-Arginine | $3.94 \times 10^2$ | DS-TWEEN-80/NaCl-Arginine-TWEEN/NaCl | $4.25 \times 10^2$ |
| TWEEN-80/NaCl(2×)-Arginine | $1.37 \times 10^3$ | TWEEN-80/NaCl(2×)-Arginine-TWEEN-80/NaCl | $1.36 \times 10^3$ |

2 × TWEEN-80/NaCl + arginine + TWEEN-80 had highest detachment, then INK + TWEEN-80 +arginine + TWEEN-80

Sample: Beef Fascia Connective Tissue

| Trial I--Inoculum: $3.62 \times 10^6$ CFU, n = 6; Trial II--Inoculum: $3.62 \times 10^6$ CFU, n = 6 Total CFUs in polysaccharide, Arginine, and TWEEN/NaCl rinses. | | |
|---|---|---|
| Detachment Procedure VI | Trial I CFU[1] | Trial II CFU[2] |
| Water- Arginine-TWEEN-80/NaCl | $1.95 \times 10^2$ | $1.64 \times 10^3$ |
| INK-Arginine-TWEEN-80/NaCl | $4.95 \times 10^2$ | $5.60 \times 10^2$ |
| CMC-Arginine-TWEEN-80/NaCl | $2.25 \times 10^2$ | $1.62 \times 10^2$ |
| DS-Arginine-TWEEN-80/NaCl | $2.30 \times 10^2$ | $5.60 \times 10^2$ |
| TWEEN/NaCl-Arginine-TWEEN/NaCl | not inoculated | $1.09 \times 10^3$ |

[1]INK followed by arginine followed by TWEEN/NaCl (INK + arginine + TWEEN/NaCl)detached the most number of CFUs, 2× higher than with CMC and DS and 2.5× higher than H₂O. The TWEEN/NaCl sample was not inoculated.
[2]TWEEN/NaCl + arginine + TWEEN detached more CFUs than with additional treatment of INK, CMC and DS.
Again, the differences among the protocol were less than one log CFU.

Sample: Beef Fascia Connective Tissue:

| Trial III--Inoculum: $1.905 \times 10^6$ CFU, n = 6; Trial IV--Inoculum: $1.23 \times 10^6$ CFU, n = 6 Total CFUs in polysaccharide, Arginine, and TWEEN/NaCl rinses. | | |
|---|---|---|
| Detachment Procedure VII | Trial III CFU | Trial IV CFU |
| Water- (3×) | $2.01 \times 10^2$ | $9.71 \times 10^2$ |
| INK-Arginine-TWEEN/NaCl | $1.53 \times 10^2$* | $8.9 \times 10^2$ |
| TWEEN/NaCl (3×) | $3.19 \times 10^2$ | $2.32 \times 10^3$ |

*In Trial III, one duplicate sample of the INK treated tissue had no CFUs in the water wash and arginine rinses. In Trials III and IV, rinses with TWEEN/NaCl yielded the highest number of CFUs/ml detached.

Summary of Results:

Tissues inoculated with $10^6$ CFU of *E. coli* O157:H7, retained $10^2$ to $10^3$ CFU.

*E. coli* ($10^4$) remained in the inoculum and were rinsed off in the water wash.

The detachment procedures used the combination of water, polysaccharides (INK=k-carrageenan, CMC=carboxymethylcellulose, DS=dextran sulfate), 0.05% TWEEN-80 (same as SPAN-80) mixed with 0.125N (0.7%) sodium chloride and arginine (food grade substitute of guanidine) detached $10^2$ to $10^3$ CFU of the bacteria.

CMC-TWEEN/NaCl; 3× TWEEN/NaCl/INK-arginine-TWEEN/NaCl; TWEEN/NaCl-arginine-TWEEN/NaCl showed higher detachment of the bacteria. However, the differences were less than one log CFU.

With the use of arginine, detachment effect of INK was enhanced (see Detachment Procedures IV-VI)

Any of the combinations described in the summary table may be used for detachment and may be further optimized to effect maximum detachment.

Longer exposure of contaminated tissues to the detaching agents may improve detachment efficiency.

In Trials 1 and II, INK followed by arginine followed by TWEEN/NaCl (INK+arginine+TWEEN/NaCl) detached the most CFUs, 2× higher than with CMC and DS and 2.5× higher than H₂O. The TWEEN/NaCl sample was not inoculated. TWEEN/NaCl+arginine+TWEEN detached more CFUs than with additional treatment with INK, CMC and DS.

Again, the differences in results among the protocols were less than one log CFU.

In Trial III, one duplicate sample of the INK treated tissue had no CFUs in the water, INK and arginine rinses. In Trials III and IV, rinses with TWEEN/NaCl yielded the highest number of CFUs/ml.

Inhibition and Detachment of *E. coli* O157:H7 From Inoculated Bovine Tissues

Experimental Procedure:

1. Veal fascia and connective tissues were separated from veal breast and cut up into 5×5 cm.
2. The bovine tissues were decontaminated with 20 ml 5% hydrogen peroxide for 30 min.
3. The excess peroxide was squeezed off and the tissues were transferred to stomacher bags containing to 50 ml sterile water.
4. The excess water was squeezed off from the tissues and transferred to stomacher bags containing 20 ml inhibitor solutions. [1-water; 2-0.3% INK; 3-0.3% CMC, 4-0.3% DS; TWEEN/NaCl. (INK=k-carrageenan, CMC=carboxymethylcellulose, DS=dextran sulfate)

5. *E. coli* O157:H7 was grown in 25 ml BHI broth at 37° C., overnight (16 hrs).
6. The bacteria was diluted up to $10^{-3}$ (approx. $10^{5-6}$ CFU) in buffered peptone for inoculation.
7. The excess inhibitors were squeezed off from the tissues and the latter were transferred to stomacher bags.
8. 20 ml of *E. coli* inoculum (prepared by diluting 0.1 ml of original broth to $10^{-3}$) was transferred to tissue samples.
9. The *E. coli* was allowed to attach to the tissues for 20 min at room temperature followed by overnight attachment at 4° C.
10. The bacterial population in tissue inoculum was plated and counted.
11. The tissues were transferred to stomacher bags containing 50 ml sterile water to rinse off excess bacteria.
12. The bacteria was detached by immersing the tissues sequentially in 50 ml 15% arginine, and 0.05% TWEEN-80 (same as SPAN-80) mixed with 0.9% sodium chloride.
13. The bacterial counts were measured in arginine and TWEEN/NaCl by plating in BHI agar.
14. To determine if the tissues contain residual bacteria and *E. coli* O157:H7, the tissues were cultured in 25 ml of modified *E. coli* (mEC) broth (FSIS defined), incubated overnight at 37° C.
15. The mEC cultures were plated and counted on either BHI or SMAC agars.

Number of Samples Analyzed: Each treatment (trials) had duplicate tissue samples. The culture for inoculation and the unattached bacteria in inoculated samples were plated in three dilutions on duplicate BHI agar.

| | | INHIBITION--Trial 1 Sample: Veal connective tissue | | | |
|---|---|---|---|---|---|
| | | Inoculum = $4.3 \times 10^6$ (n = 6) | | | |
| Sample # | Sample Treatment | Excess bacteria in inoculum | Water Rinse | Arginine Detachment | TWEEN-80/NaCl Detachment |
| 1 | $H_2O$-EC-$H_2O$-Arginine-TWEEN-80/NaCl | $2.5 \times 10^3$ | 1 | $4.63 \times 10^1$ | 0 |
| 2* | INK-EC-$H_2O$-Arginine-TWEEN-80/NaCl | $4.93 \times 10^3$ | 2 | $3.71 \times 10^1$ | 0 |
| 3 | CMC-EC-$H_2O$-Arginine-TWEEN-80/NaCl | $5.08 \times 10^3$ | 2 | $4.17 \times 10^1$ | 0 |
| 4 | DS-EC-$H_2O$-Arginine-TWEEN-80/NaCl | $2.92 \times 10^3$ | 1 | $3.71 \times 10^1$ | $2.78 \times 10^1$ |
| 5 | TWEEN-80/NaCl-EC-$H_2O$-Arginine-TWEEN-80/NaCl | $21.2 \times 10^3$ | 2 | $6.95 \times 10^1$ | $1.85 \times 10^1$ |

*One INK duplicate sample exhibited pinpoint growth in cultured mEC broth indicating that microorganisms in tissues were not *E. coli* O157:H7. One CFU of *E. coli* O157:H7 was detected in sample 4b tissue when cultured in mEC (modified *E. coli*) broth (selective for *E. coli*). In all samples (Numbers 1–5) *E. coli* O157:H7 was recovered in water and arginine washes but were not recovered with TWEEN/NaCl wash in Samples 1, 2 and 3.

EC = *E. coli*

Sample 1 = $H_2O$-EC-$H_2O$-Arg-TWEEN-80/NaCl = $H_2O$ followed by EC followed by $H_2O$ followed by Arginine followed by TWEEN-80/NaCl

| | | INHIBITION--Trial 2 Sample: Veal connective tissue | | | | |
|---|---|---|---|---|---|---|
| | | Inoculum = $8.0 \times 10^6$ (n = 6) | | | | |
| Sample # | Sample Treatment | Excess bacteria in inoculum | Water Rinse | Arginine Detachment Rinse | TWEEN-80/NaCl Detachment Rinse | Total Rinses $H_2O$-Arginine-TWEEN-80/NaCl |
| 1 | $H_2O$-EC-$H_2O$-Arginine-TWEEN-80/NaCl | $1.42 \times 10^2$ | $4.63 \times 10^2$ | $1.40 \times 10^2$ | $5.1 \times 10^1$ | $6.54 \times 10^2$ |
| 2 | INK-EC-$H_2O$Arginine-TWEEN-80/NaCl | $1.69 \times 10^4$ | $1.85 \times 10^2$ | $4.17 \times 10^1$ | $3.7 \times 10^1$ | $2.64 \times 10^2$ |
| 3 | CMC-EC-$H_2O$-Arginine-TWEEN-80/NaCl | $1.63 \times 10^4$ | 0 | $3.71 \times 10^1$ | $2.78 \times 10^1$ | $6.49 \times 10^1$ |
| 4 | DS-EC-$H_2O$-Arginine-TWEEN-80/NaCl | $9.99 \times 10^3$ | $3.69 \times 10^2$ | $1.27 \times 10^2$ | $5.56 \times 10^1$ | $5.52 \times 10^2$ |
| 5 | TWEEN-80/NaCl-EC-$H_2O$-Arginine-TWEEN-80/NaCl | $21.2 \times 10^4$ | $1.85 \times 10^2$ | $7.41 \times 10^1$ | $3.70 \times 10^1$ | $2.96 \times 10^2$ |

Tissues cultured in mEC broth have contaminants in samples 1-4. Sample 5a had no bacteria while sample 5b had 1 CFU/ml. *E. coli* was not detected in all samples except in 5b.

C. 0.05% TWEEN-80-0.9% NaCl
D. 0.3% Carboxymethyl cellulose (CMC)
E. 0.3% Dextran Sulfate (DS)

INHIBITION--Trial 3, Sample: Veal connective tissue
Inoculum = $4.315 \times 10^6$ (n = 6)

| Sample # | Sample Treatment | Excess bacteria in inoculum | Water Rinse | Arginine Detachment Rinse | TWEEN/NaCl Detachment Rinse | Total Rinses $H_2O$-Arginine-TWEEN-80/NaCl |
|---|---|---|---|---|---|---|
| 1 | $H_2O$-EC-$H_2O$-Arginine-TWEEN-80/NaCl | $1.18 \times 10^4$ | 0 | $4.61 \times 10^1$ | $3.71 \times 10^1$ | $8.33 \times 10^1$ |
| 2 | INK-EC-$H_2O$-Arginine-TWEEN-80/NaCl | $7.65 \times 10^3$ | 0 | $2.31 \times 10^1$ | 0 | $2.33 \times 10^1$ |
| 3 | CMC-EC-$H_2O$-Arginine-TWEEN-80/NaCl | $3.52 \times 10^3$ | 0 | $2.77 \times 10^1$ | $1.85 \times 10^1$ | $4.62 \times 10^1$ |
| 4 | DS-EC-$H_2O$-Arginine-TWEEN-80/NaCl | $8.59 \times 10^2$ | $1.85 \times 10^2$ | $6.50 \times 10^1$ | $4.16 \times 10^1$ | $2.92 \times 10^2$ |
| 5 | TWEEN-80/NaCl-EC-$H_2O$-Arginine-TWEEN-80/NaCl | $4.61 \times 10^3$ | 0 | $7.42 \times 10^1$ | $2.77 \times 10^1$ | $1.02 \times 10^2$ |

Samples treated with INK (Sample 2) and CMC (Sample 3) showed greater inhibition vs those samples treated with water (Sample 1), DS (Sample 4) and TWEEN/NaCl (Sample 5) shown by the lower number of CFUs recovered in the "Total rinses".
Tissue samples cultured in mEC broth demonstrated no *E. coli* growth in samples 1, 2, 4 and 5. One replicate sample (3a) of sample 3 treated with CMC had one CFU/ml of *E. coli*.

Summary of Results in the Inhibition/detachment Experiments:

These data demonstrate the effectiveness of carrageenans, arginine, TWEEN-80/NaCl treatments.

In Trial 1, one K-carrageenan (INK) duplicate sample exhibited pinpoint growth in cultured mEC broth indicating that microorganisms in tissues were not *E. coli* O157:H7. One CFU of *E. coli* O157:H7 was detected in sample 4b tissue when cultured in mEC broth. In all samples (Numbers 1-5) *E. coli* O157:H7 was recovered in water and arginine washes but were not recovered with TWEEN/NaCl wash in Samples 1, 2 and 3.

In Trial 2, tissues cultured in mEC broth have contaminants in samples 1-4. Sample 5a had no bacteria while sample 5b had 1 CFU/ml.

In Trial 3, samples treated with INK (Sample 2) and CMC (Sample 3) showed greater inhibition vs those samples treated with water (Sample 1), DS (Sample 4) and TWEEN/NaCl (Sample 5) shown by the lower number of CFUs recovered in the "Total rinses".

Tissue samples cultured in mEC broth demonstrated no *E. coli* growth in samples 1, 2, 4 and 5. One replicate sample (3a) treated with CMC had one CFU/ml of *E. coli*. These inhibition and detachment procedures prevented the attachment of most *E. coli* to the veal connective tissues and were detached with sequential rinses in water, arginine and NaCl/non-ionic surfactant solutions.

Inhibition of *Salmonella Typhimurium* Attachment to Chicken Skin by the Polysaccharides and Detachment with Water, Arginine and TWEEN-80/NaCl.

Method:
1. Fresh chicken skin was cut into 24-25 cm² surface.
2. The tissues were immersed in 5% hydrogen peroxide to inactivate the natural flora and followed by washing in 50 ml water.
3. The samples were transferred to stomacher bags and coated with the following:
   A. Water wash
   B. 0.3% K-carrageenan (INK)
   C. 0.05% TWEEN-80-0.9% NaCl
   D. 0.3% Carboxymethyl cellulose (CMC)
   E. 0.3% Dextran Sulfate (DS)
4. The samples were transferred to fresh stomacher bags containing 50 ml water to remove excess inhibitors. (this step was used in Trial 3)
5. *Salmonella typhimurium* (ST) was inoculated on the outer skin surface using 0.1 ml of $10^4$ cfu/ml and spreading with a "hockey stick" glass rod.
6. ST was allowed to grow and attach for 1 hr at room temperature followed by overnight incubation at 4° C.
7. The samples were transferred to stomacher bags for detachment using the following:
   A. Water wash (3×)
   B. 0.75M Arginine and followed by 2× with 0.05% TWEEN-80-0.9% NaCl
   C. 0.05% TWEEN-80-0.9% NaCl (3×)
   D. 0.75M Arginine and 2×0.05% TWEEN-80-0.9% NaCl
   E. 0.75M Arginine and 2×0.05% TWEEN-80-0.9% NaCl
8. The tissue samples were then plated directly on XLT4 agar with the outer skin side touching the agar surface. Samples were incubated at 37° C. overnight.

Results: The tissues were divided into 4 quadrants and the number of quadrants with black spots were reported as + if only one quadrant has black spots, ++ if two quadrants have black surfaces, etc. Treatment of the tissues with INK (kappa-carrageenan) followed by arginine and TWEEN/NaCl showed negative results in 3 out of four samples compared to water wash, DS (dextran sulfate), CMC (carboxymethylcellulose) or TWEEN and NaCl washes. These treatments suggest that carrageenan had greater inhibition effects than water wash alone, dextran sulfate/arginine/TWEEN-80-NaCl or carboxy-methyl-cellulose/arginine/15:21 TWEEN-NaCl treatments. See Table 1.

TABLE 1

| Black spots (colonies) on XLT4 agar. | | | | |
|---|---|---|---|---|
| Treatment | Trial 1A | Trial 1B | Trial 2A | Trial 2B |
| A. Water wash (4×) | ++++ | + (trace) | +++ | +++ |
| B. INK-Arginine-TWEEN-80 | − (neg.) | − (neg.) | +++ | − (neg.) |
| C. TWEEN-80/NaCl (4×) | ++++ | ++++ | 2 | − (neg.) |

TABLE 1-continued

Black spots (colonies) on XLT4 agar.

| Treatment | Trial 1A | Trial 1B | Trial 2A | Trial 2B |
|---|---|---|---|---|
| D. CMC-Arginine-TWEEN-80 | +++ | +++ | ++++ | 2 |
| E. DS-Arginine-TWEEN-80 | 1 | 1 | – (neg.) | +++ |

(Black colonies or spots indicate positive for *Salmonella*. The number of + indicate the number of quadrants if the tissue was segmented to 4 parts.)

TABLE 1

Trial 3. Black spots (colonies) on XLT4 agar.

| Treatment | Trial 3A | Trial 3B |
|---|---|---|
| A. Water wash (4×) | +++ | + ++ |
| B. INK-Arginine-TWEEN-80 | <+ | <+ |
| C. TWEEN-80/NaCl (4×) | ++++ | +++ |
| D. CMC-Arginine-TWEEN-80 | ++++ | 3 |
| E. DS-Arginine-TWEEN-80 | ++++ | 0 |

Black colonies or spots indicate positive for *Salmonella*. The number of + indicate the number of quadrants if the tissue was segmented to 4 parts.)

Treatment of the tissues with INK (kappa-carrageenan) inhibited *Salmonella* attachment greater than water wash, DS (dextran sulfate), CMC (carboxy methyl cellulose) or TWEEN-80 and NaCl washes. These treatments were followed by arginine and TWEEN/NaCl).

Figure 7A:
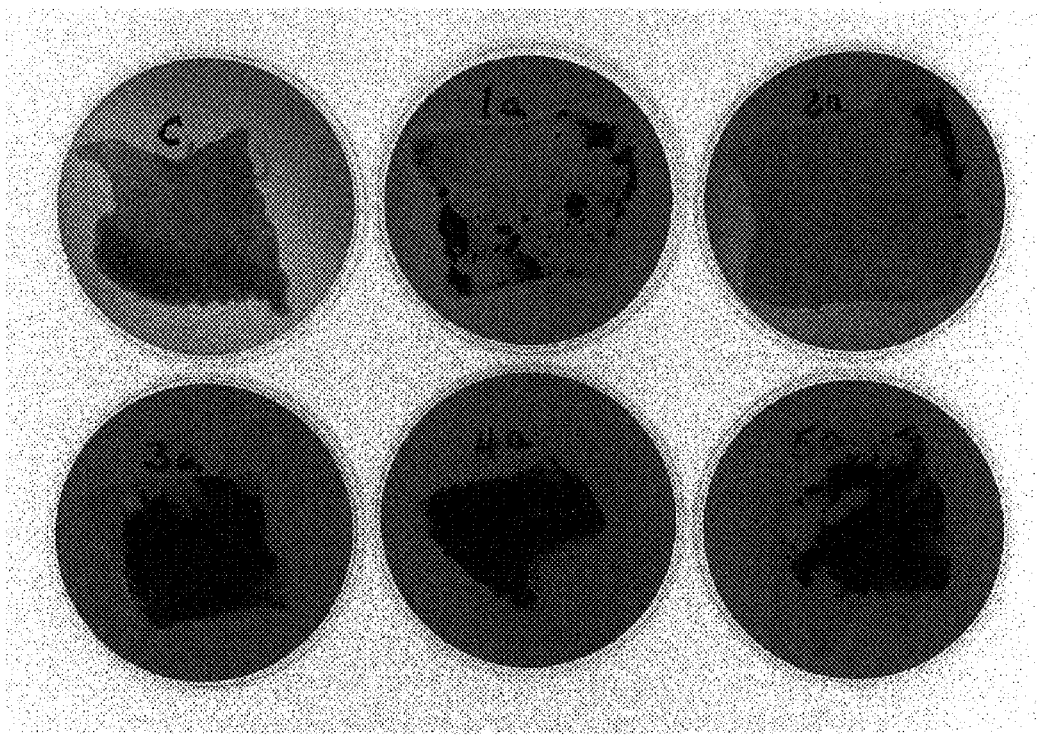
FIGS. 7A and B respectively show photos of chicken skin inoculated with *Salmonella* from Trial 3A and 3B (described in Table 1: Trial 3 which is immediately before paragraph 0063 below.
Figure 7B:
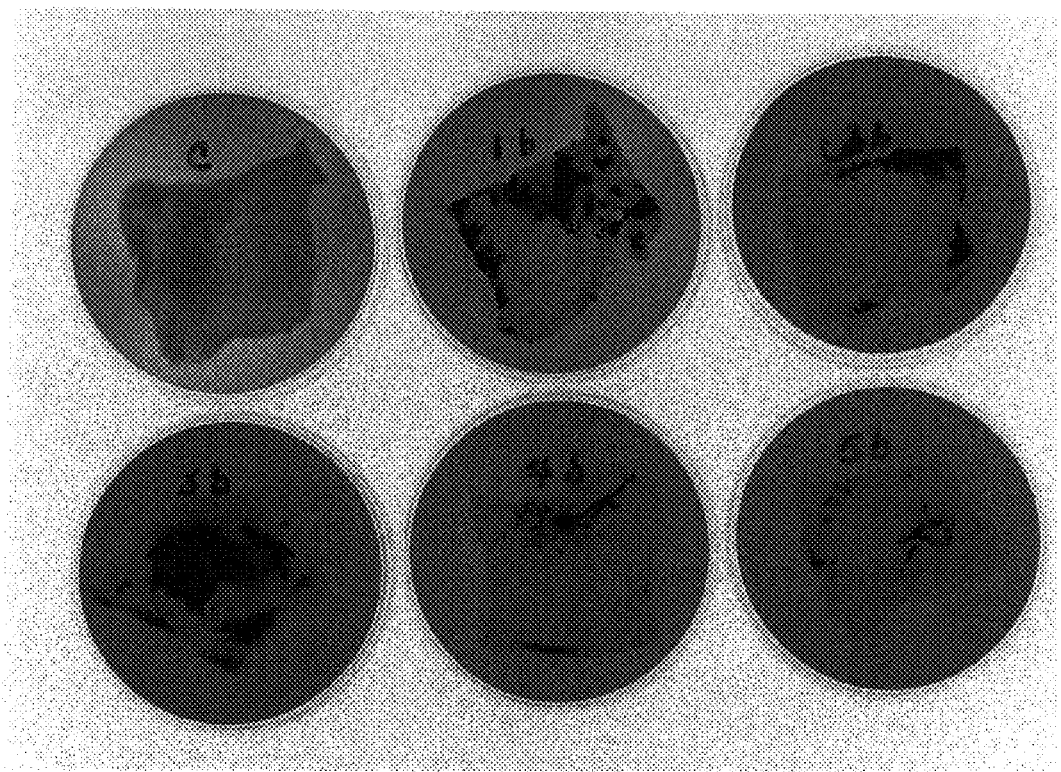
Figure 8A:
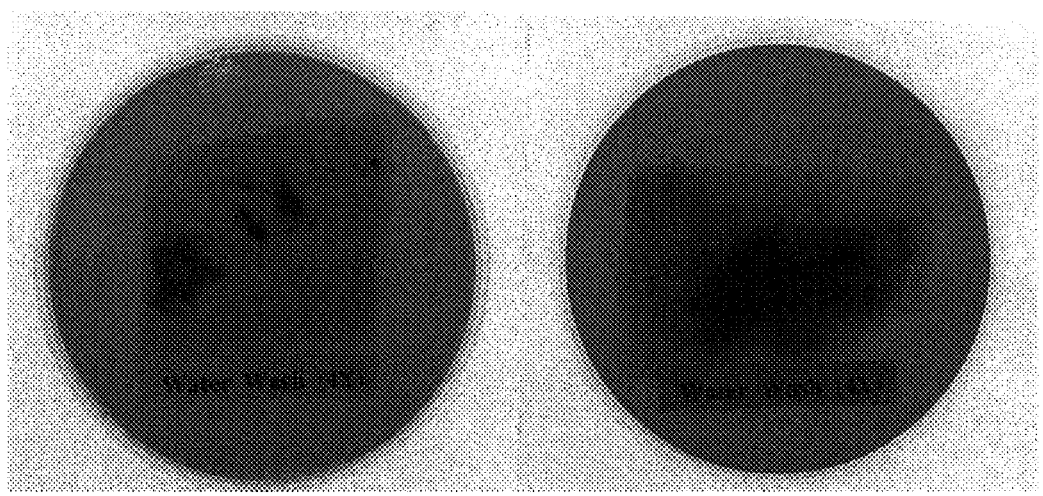
FIGS. 8A-E respectively show photos of pork inoculated with *Salmonella* from the trials A-E described in paragraph 65 below.
Figure 8B:
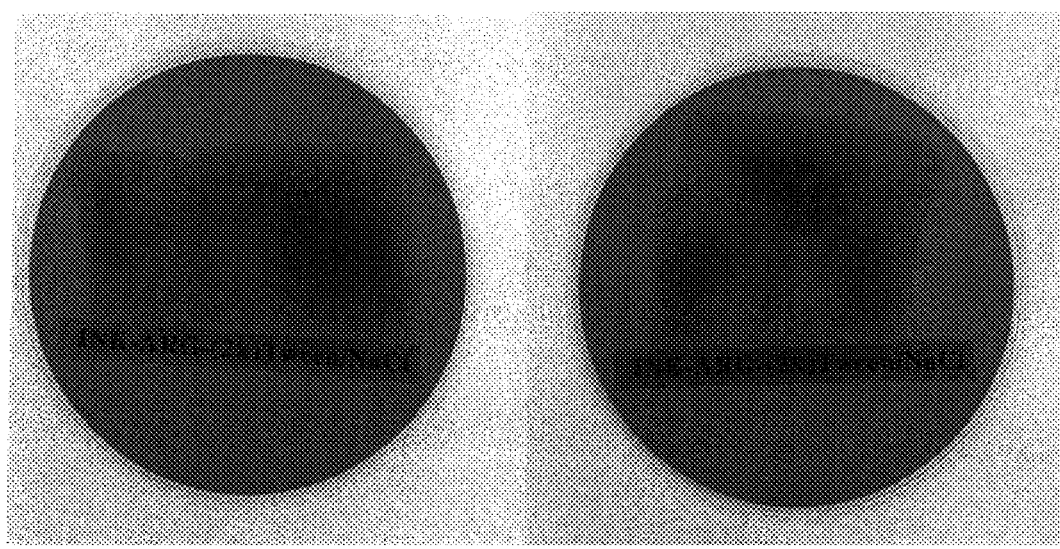
Figure 8C:
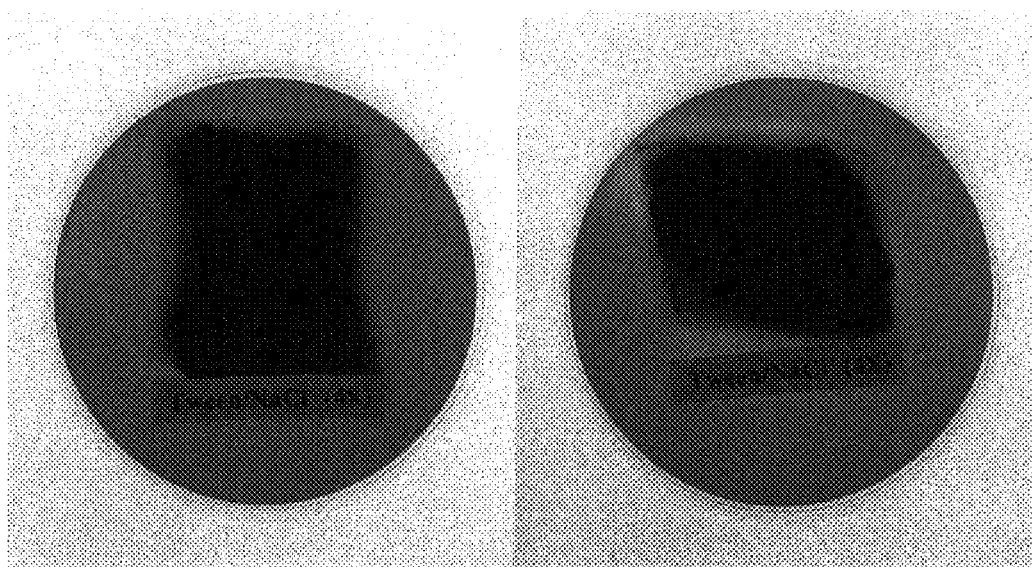
Figure 8D:
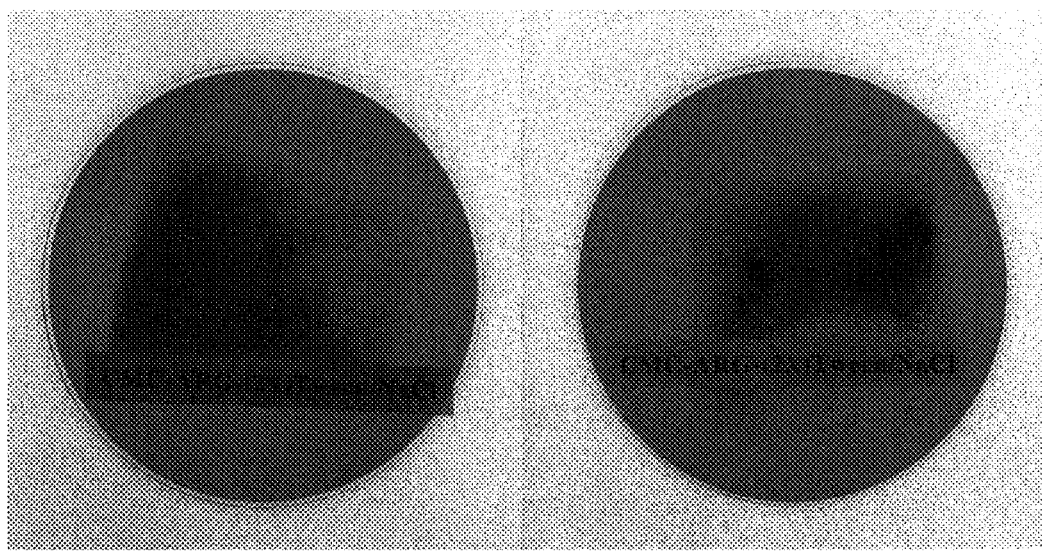
Figure 8E:
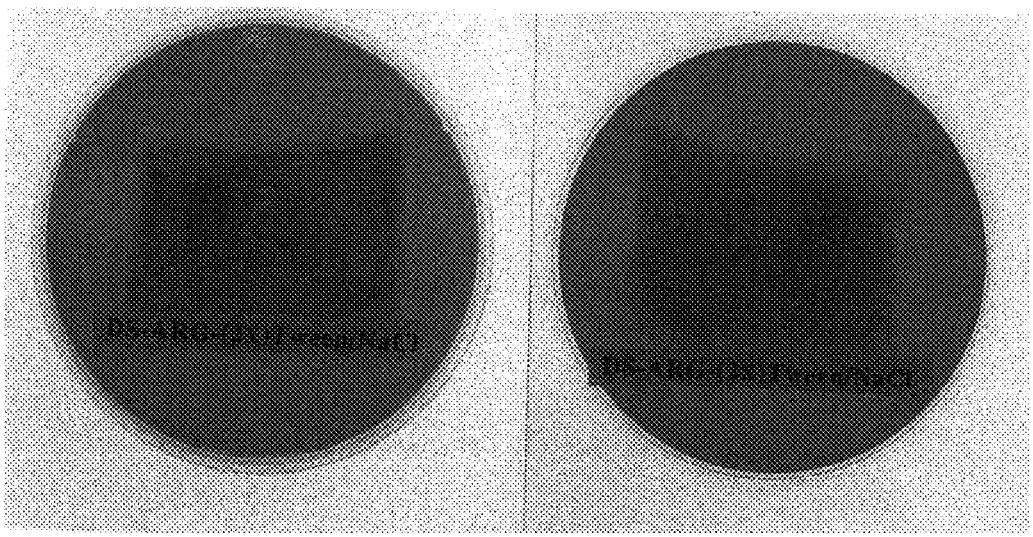

FIGS. 7A and B show the results from Trial 3A and 3B. The carrageenan treated samples (1a, 1b) followed by arginine and TWEEN-80 washes showed the least contamination with *Salmonella*. The contamination was only at the edges of the samples. This may be due to the curling of the edges during the test, the edges may not have gotten fully coated with carrageenan. "C" is the control sample and was not inoculated with *Salmonella*.

Detachment of *Salmonella Typhimurium* Inoculated to Pork Skin.
1. Fresh pig skin was cut into 24-25 cm² surface.
2. The tissues were immersed in 5% hydrogen peroxide to inactivate the natural flora.
3. *Salmonella typhimurium* (ST) was inoculated on the outer skin surface with 0.1 ml of $10^6$ cfu/ml.
4. ST was allowed to grow and attach for 1 hr at room temperature followed by overnight incubation at 4° C.
5. The samples were transferred to stomacher bags for detachment using the following:
   A. Water wash (4×)
   B. 0.3% K-carrageenan (INK), followed by 0.75M arginine followed by 2× with TWEEN-80-NaCl (INK-ARG-2×-TWEEN/NaCl)
   C. 0.05% TWEEN-80-0.9% NaCl (4×) (TWEEN/NaCl 4×)
   D. 0.3% carboxymethyl cellulose (CMC); 0.75 arginine; and 2×0.05% TWEEN-80-0.9% NaCl (CMC-ARG-2× TWEEN/NaCl)
   E. 0.3% Dextran Sulfate (DS); 0.75M arginine; and 2×0.05% TWEEN-80-0.9% NaCl (DS-ARG-2× TWEEN/NaCl)
6. The tissue samples were then plated directly on XLT4 agar with the skin side touching the agar surface. Samples were incubated at 37° C. overnight.

Results: These results are shown in attached photographs (FIGS. 8A-E). The results indicated that ST remained on the samples treated with water (4×) and CMC-Arginine-TWEEN-80/NaCl. Samples treated with TWEEN-80-NaCl alone apparently enhanced the attachment of ST. Samples treated with carrageenan-arginine-TWEEN/NaCl and Dextran sulfate-arginine-TWEEN/NaCl apparently detached ST from pork skin surface.

Extraction/isolation of Natural *E. coli*, Coliforms and *Salmonella* spp. from Ground Chicken Purchased from a Local Market.

Sample Preparation:
1. Aseptically mix ground chicken by mashing manually to make a homogenous mix.
2. Make a ball and flatten the ground turkey into a round shape on a sterile cutting board.
3. Then cut four ways and transferred into 4 sterile bags. Take the opposite quarters for analysis and store the other quarters at –20° C.
4. Using a sterile spatula weigh out 25 g into a stomacher bag.
5. Pre-coat samples (#3 and 4) with 25 ml 0.3% INK, 30 min. at room temperature.
6. Squeeze fluid from chicken and transfer coating fluid to a sterile 250 ml flask. Store on ice.
7. Rinse 1 Add the following rinse materials to ground chicken samples and homgenize with a stomacher for min at low speed.
   #1ab) 100 ml butterfields buffer
   #2ab) 100 ml PBST
   #3ab) 100 ml PBST
   4ab) 100 ml arginine
8. Extract, squeeze fluids and transfer fluids to 250 ml flasks. Store on ice.
9. Rinse 2 Add the following rinse materials to ground chicken samples and homgenize with a stomacher for 1 min at low speed.
   1ab) 100 ml butterfields buffer
   2ab) 100 ml PBST
   3ab) 100 ml PBST
   4ab) 100 ml PBST
10. Extract, squeeze fluids and transfer fluids to 250 ml flasks. Store on ice.
11. Pool liquids collected in steps 6, 8 and 10.
12. Adjust volume to 250 ml with Butterfields Buffer.

Testing for Coliform and *E. coli*
13. Take aliquots of pooled rinses from Samples #1-4 and dilute to $10^0$, $10^{-1}$, $10^{-2}$.
14. Test for coliform and *E. coli* using 3M Petrifilm by transferring 1 ml of diluted samples over the gel as directed by the manufacturer.
15. Incubate gel film for 24 hr at 37° C.

16. Examine results for gas producing red (coliform) and blue colonies (confirmed *E. coli*) and blue colonies without gas (presumptive *E. coli*).

Determine Detachment of *Salmonella* spp. from Ground Chicken by Culturing in Non-selective and Selective Broth and Detection with XLT4 Agar.

Treat Samples as in Steps 1-12:

Non-selective Enrichment for *Salmonella:*

17. Take out 30 ml aliquot of pooled liquid wash separately into four sterile 125 ml flask.
18. Add 30 ml of double strength Buffered Peptone Water (BPW).
19. Incubate flasks at 35° C.+/−1° C. for 20-24 hr.
20. Dilute inoculum at $10^{-2}$, $10^{-3}$, $10^{-4}$ and plate 50 μl of of samples over XLT4 agar.
21. Incubate at 35+/−1° C. for 22-24 hrs. Examine for black coloniesor yellow to red wtih black centers [sulfur producing *Salmonella* strains]; yellow-pink indicate the presence of non sulfur producing *Salmonella* strains.
22. Reincubate negative plates. Re-examine next day.

Selective Enrichment for *Salmonella* in TT Broth and RV Broth

23. Transfer 0.5 ml of samples enriched in non-selective broth to 10 ml of TT broth.
24. Transfer 0.1 ml of samples enriched in non-selective broth to 10 ml of RV broth.
25. Incubate at 42° C. for 22-24 hrs.
26. Dilute to $10^{-4}$, $10^{-5}$, $10^{-6}$. Plate on XLT4 Agar in duplicate per sample.
27. Incubate at 35+/−1° C. for 22-24 hrs. Examine for black or red colonies.
28. Reincubate negative plates. Re-examine next day.

Detection of *Salmonella* Spp. from Ground Chicken Extracted and Isolated by Inventive Rinse Agents

| Trial 1 Sample No. | Ground chicken Treatment | *Salmonella* spp. Non-selective | *Salmonella* spp. TT Broth | *Salmonella* spp. RV Broth |
|---|---|---|---|---|
| 1a | BB 2× | − | | + |
| 1b | BB 2× | − | | + |
| 2a | PBST 2× | − | + | + |
| 2b | PBST 2× | − | | + |
| 3a | INK-PBST-PBST | − | | + |
| 3b | INK-PBST-PBST | | | + |
| 4a | INK-Arg-PBST | | + | |
| 4b | INK-Arg-PBST | − | + | |

| Trial II Sample No. | Ground chicken Treatment | *Salmonella* spp. Non-selective | *Salmonella* spp. TT Broth | *Salmonella* spp. RV Broth |
|---|---|---|---|---|
| 1a | BB 2× | − | | |
| 1b | BB 2× | − | + | + |
| 2a | PBST 2× | − | + | + |
| 2b | PBST 2× | − | + | |
| 3a | INK-PBST-PBST | − | + | |
| 3b | INK-PBST-PBST | | + | |
| 4a | INK-Arg-PBST | − | | + |
| 4b | INK-Arg-PBST | − | | + |

| Trial III Sample No. | Ground chicken Treatment | *Salmonella* spp. Non-selective | *Salmonella* spp. TT Broth | *Salmonella* spp. RV Broth |
|---|---|---|---|---|
| 1a | BB 2× | − | | |
| 1b | BB 2× | − | | |
| 2a | PBST 2× | − | +p | |
| 2b | PBST 2× | − | +P | |
| 3a | INK-PBST-PBST | − | | |
| 3b | INK-PBST-PBST | | +p | |
| 4a | INK-Arg-PBST | − | | |
| 4b | INK-Arg-PBST | − | | |

Results: These samples did not test positive for *Salmonella* after enrichment of pooled rinse materials in non-selective broth. However, when enriched in selective broths (TT and RV) *Salmonella* spp. were invaiably detected in all test samples in Trials I and II. In Trials 1, these results indicate that *Salmonella* was present in the ground chicken samples as injured cells and were revived in selective enrichment. In Trial III, pink colonies (+p) were detected in samples, 2a, 2b and 3a, indicating presence of non-sulfur producing *Salmonella*. Blank data also indicate no detectable *Salmonella*.

Summary Data on Detachment of *E. coli* and Coliforms from Ground Chicken and their Detection with Coliform/*E. coli* Petrifilm test.

| Sample No. | Treatment | Trial I Coliform | Trial I *E. coli* | Trial II Coliform | Trial II *E. coli* | Trial III Coliform | Trial III *E. coli* |
|---|---|---|---|---|---|---|---|
| 1a | BB 2× | 64, 9, 1 | | 19, 14, 1 | 6 | 41, 4 | 13 |
| 1b | BB 2× | 56, 2 | | 13, 6, 1 | 2, 2 | 35, 5 | 7, 1 |
| 2a | PBST 2× | 52, 4 | | 15, 3 | 2, 1 | 39, 2 | 6 |
| 2b | PBST 2× | 46 | | 80, 1 | 4, 3 | 37, 2, 1 | 1 |
| 3a | INK-PBST-PBST | 76, 1 | | 160, 1, 1 | 5 | 37, 1 | 5 |
| 3b | INK-PBST-PBST | 39, 5 | | 42, 4, 1 | 2, 2 | 48, 5 | 9, 2 |
| 4a | INK-Arg-PBST | 28, 4, 1 | | 13, 3 | 31 | 4 | 1 |
| 4b | INK-Arg-PBST | 36, 2 | | 6 | 2 | 1 | 1 |

Sample treatment: BB=Butterfield's buffer; PBST=phosphate buffer containing 0.9% sodium chloride and 0.05% TWEEN-80; INK=kappa-carrageenan; arg=arginine. Each sample was plated at three dilutions, $10^0$, $10^{-1}$, and $10^{-2}$. One ml sample was applied on Petrifilm. The manufacturer's guidelines and interpretation of results were followed. Results indicated by single numbers are detected at one dilution, typically in undiluted sample washes ($10^0$). When 2 are reported, the bacteria are detected at $10^{-0}$ and $10^{-1}$, and $10^0$, $10^{-1}$, and $10^{-2}$, The CFU reported indicate actual number per Petrifilm test (based on 1 ml sample) and are not adjusted to sample dilution. Samples without numbers indicate that coliform or *E. coli* was not detected. The coliforms were indicated by red colonies with gas bubbles. Confirmed *E. coli* were indicated by blue to red colonies with gas bubbles.

These results indicate that the coliform and *E. coli* were randomly distributed in the samples and were detached and isolated by the 4 treatments. However, the highest number of detached Coliforms were detected when the samples were pre-coated with carrageenans and rinsed with PBST. In Trials I and II, the highest number of *E. coli* were detected in Samples 1a and 4a. In Trial III, non-sulfur producing *Salmonella* strains were detected as indicated by pink colonies and pink colonies with cream centers.

Extraction and Isolation of Natural Bacteria and *Salmonella* spp. from Ground Turkey Sample Preparation 1. Aseptically mix ground turkey by mashing manually to make a homogenous mix.
2. Make a ball and flatten the ground turkey into a round shape on a sterile cutting board.
3. Then cut four ways and store separately. Take the opposite quarters for analysis.
4. Using a sterile spatula weigh out 25 g into a stomacher bag.
5. Pre-coat sample #3 only with 25 ml 0.3% INK, 30 min. at room temperature.
6. Rinse 1—Add the following rinse materials to ground turkey samples and homogenize with a stomacher for 1 min at low speed.
   #1ab) 125 ml Butterfield's Buffer
   #2ab) 125 ml 0.3% INK in BB
   #3ab) 100 ml PBST
7. Extract, squeeze fluids and transfer fluids to 250 ml flasks. Store on ice.
8. Rinse 2. Add 100 ml of the rinse agents described in Step 6.
9. Extract turkey with a stomacher at low speed for 1 min. Transfer and pool liquids as described in step 6.
10. Adjust volume to 225 ml with Butterfield's Buffer.

Testing for Coliform and *E. coli*

11. Take aliquots from Samples #1-3 and dilute to $10^0$, $10^{-1}$, $10^{-2}$.
12. Test for coliform and *E. coli* using 3M Petrifilm by transferring 1 ml of diluted samples over the gel as directed by the manufacturer.
13. Incubate gel film for 24 hr at 37° C.
14. Examine results for gas producing red (coliform) and blue colonies (confirmed *E. coli*) and blue colonies without gas (presumptive *E. coli*).

Determine detachment of *Salmonella* spp. from ground turkey by culturing in non-selective and selective broth and detection with XLT4 Agar.

Treat Samples as in Steps 1-10:

Non-selective Enrichment for *Salmonella*:

15. Take out 30 ml aliquot of pooled liquid wash separately into four sterile 125 ml flask.
16. Add 30 ml of double strength Buffered Peptone Water (BPW).
17. Incubate flasks at 35° C.+/−1° C. for 20-24 hr.
18. Dilute inoculum at $10^{-2}$, $10^{-3}$, $10^{-4}$ and plate 50 µl of of samples over XLT4 agar.

Selective Enrichment for *Salmonella*: in TT Broth and RV Broth

19. Transfer 0.5 ml of samples enriched in non-selective broth to 10 ml of TT broth.
20. Transfer 0.1 ml of samples enriched in non-selective broth to 10 ml of RV broth.
21. Incubate at 42° C. for 22-24 hrs.
22. Plate on XLT4 Agar. Duplicate plates per sample. Dilute to $10^{-4}$, $10^{-5}$, $10^{-6}$.
23. Incubate at 35+/−1° C. for 22-24 hrs.
24. Reincubate negative plates. Re-examine next day.
25. Examine for black or red colonies.

Reagents:

BB=Butterfield's Buffer: 0.5 mM Phosphate buffer, pH 7.2. [Ref. FDA Bacteriological Analytical Manual]. PBST=Phosphate Buffered Saline with TWEEN-80 or SPAN-80: 0.5 mM Phosphate buffer, 0.9% NaCl, 0.05% TWEEN-80. INK=Carrageenan solutions (0.3%) are prepared aseptically by heating sterile water to 70° C. Then add the carrageenan by tapping the powder into the liquid. Break the lumps by using a sterile rod or homogenizer. INK in BB=Carrageenan solutions (0.3%) are prepared aseptically by heating sterile BB to 70° C. TT Broth=Tetrathionate [USDA FSIS Microbiology Guidebook.]. RV Broth=Rappaport Vassiliadis [USDA FSIS Microbiology Guidebook].

Detection of *Salmonella* Spp. from Ground Turkey Extracted and Isolated by Inventive Rinse Agents

| Trial 1 Sample No. | Ground turkey Treatment | Salmonella spp. Non-selective | Salmonella spp. TT Broth | Salmonella spp. RV Broth |
|---|---|---|---|---|
| 1a | BB 2× | − | | |
| 1b | BB 2× | | + | |
| 2a | INK in BB 2× | − | | |
| 2b | INK in BB 2× | | + | + |
| 3a | INK-PBST-PBST | − | | |
| 3b | INK-PBST-PBST | | | |

| Trial 2 Sample No. | Ground turkey Treatment | Salmonella spp. Non-selective | Salmonella spp. TT Broth | Salmonella spp. RV Broth |
|---|---|---|---|---|
| 1a | BB 2× | − | − | − |
| 1b | BB 2× | − | − | − |
| 2a | INK in BB 2× | − | − | − |
| 2b | INK in BB 2× | − | − | − |
| 3a | INK-PBST-PBST | − | − | − |
| 3b | INK-PBST-PBST | − | − | + |

| Trial 3 Sample No. | Ground turkey Treatment | Salmonella spp. Non-selective | Salmonella spp. TT Broth | Salmonella spp. RV Broth |
|---|---|---|---|---|
| 1a | BB 2× | − | + | + |
| 1b | BB 2× | − | + | + |
| 2a | INK in BB 2× | − | + | + |
| 2b | INK in BB 2× | − | + | + |
| 3a | INK-PBST-PBST | − | + | + |
| 3b | INK-PBST-PBST | − | + | + |

| Sample No. | Treatment | Trial I Coliform | Trial I E. coli | Trial II Coliform | Trial II E. coli | Trial III Coliform | Trial III E. coli | Trial IV Coliform | Trial IV E. coli |
|---|---|---|---|---|---|---|---|---|---|
| 1a | BB 2× | 1 | | 1 | | | | 2 | 1 |
| 1b | BB 2× | | | 1 | 2 | 1 | | | |
| 2a | INK in BB 2× | 2 | | 5 | | | 2 | 2 | 3 |
| 2b | INK in BB 2× | | | 1, 1 | 3 | 1 | | 2 | 4 |
| 3a | PBST 2× | | | 1 | 7 | 2 | | 3 | |
| 3b | PBST 2× | | 3 | 1, 1 | 1, 1 | | 1 | | 3 |

| Trial 4 Sample No. | Ground turkey Treatment | Salmonella spp. Non-selective | Salmonella spp. TT Broth | Salmonella spp. RV Broth |
|---|---|---|---|---|
| 1a | BB 2× | − | + | + |
| 1b | BB 2× | − | + | + |
| 2a | INK in BB 2× | − | + | |
| 2b | INK in BB 2× | − | + | + |
| 3a | INK-PBST-PBST | − | + | + |
| 3b | INK-PBST-PBST | − | + | + |

Results: These samples did not test positive for *Salmonella* after enrichment of rinse materials in non-selective broth. However, when enriched in selective broths (TT and RV) *Salmonella* spp. were detected in all test samples in Trials 3 and 4. In Trials 1, *Salmonella* was detected in 1b and 2b and in Trial 2, Sample 3b indicated positive. These results indicate that *Salmonella* were present in the ground turkey samples as injured cells and were revived in selective enrichment.

Modified Rinse Procedures. Samples 3 and 4 were Precoated with 0.3% INK for 30 min at Room Temperature.

| Trial 1 Sample No. | Ground turkey Treatment | Salmonella spp. Non-selective | Salmonella spp. TT Broth | Salmonella spp. RV Broth |
|---|---|---|---|---|
| 1a | BB 2× | − | + | |
| 1b | BB 2× | − | − | |
| 2a | PBST 2× | − | + | |
| 2b | PBST 2× | + | + | + |
| 3a | INK-PBST-PBST | + | + | |
| 3b | INK-PBST-PBST | + | + | + |
| 4a | INK-ARG-PBST | + | + | |
| 4b | INK-ARG-PBST | + | + | |

The ground turkey samples in this modified procedure showed positive results for *Salmonella* spp. in samples 2, 3, and 4 when treated with the inventive surface rinse materials and enriched in non-selected broth. These results indicated that *Salmonella* spp. proliferated in the non-selective culture. *Salmonella* spp. was not detected in Sample 1a and 1b when extracts were enriched in non-selective and RV enrichments broth. Blank date indicate no detectable *Salmonella*.

Summary Data on Detachment of *E. coli* and Coliforms From Ground Turkey and Their Detection with Coliform/*E. coli* Petrifilm Test.

Sample treatment, BB=Butterfield's buffer; PBST=phosphate buffer containing 0.9% sodium chloride and 0.05% TWEEN-80; INK=kappa-carrageenan. Each sample was plated at three dilutions, $10^0$, $10^{-1}$, and $10^{-2}$ and applying 1 ml sample aliquots on Petrifilm. The manufacturer's guidelines and interpretation of results were followed. Results indicated by single numbers are detected at one dilution, typically in undiluted sample washes ($10^0$). When two numbers are reported, the bacteria are detected at $10^0$ and $10^{-1}$. The CFU reported indicate actual number per Petrifilm test (based on 1 ml sample) and are not adjusted to sample dilution. Samples without numbers indicate that coliform or *E. coli* were not detected. The coliforms were indicated by red colonies with gas bubbles. Confirmed *E. coli* were indicated by blue to red colonies with gas bubbles.

These results indicate that the treated samples (#2 and 3) showed enhanced detachment of *E. coli*. Blank data indicate no detectable coliform or *E. coli*. In trial I, *E. coli* was recovered in samples treated by the inventive rinse agents (#2 and #3). The original ground turkey sample in Trial III was stored for 8 days at 4° C. and then treated with the inventive rinse agents to detach the bacteria followed by analysis with *E. coli*/Coliform Petrifilm. Coliform recovery was highest in samples treated in 2b, 3a, and 3b resulting in 81, 86 and 89 cfu/ml while 1a, 1b and 2a had 74, 24 and 61 cfu/ml. The numbers indicated in bold show the highest recovery of bacteria from the experimental treatment with inventive rinse materials.

Detachment of *Salmonella* spp, *E. coli*/and Coliforms from Whole Chicken Using the Inventive Rinse Materials.

The following procedure is a modification of the FSIS procedure for rinsing a whole chicken (USDA/FSIS Microbiology Guidebook, 3rd Edition) and adapted to whole chicken legs (drumstick and thigh). The chicken was purchased from a local market.

Sample Preparation
1. Prepare four duplicate samples (#1, #2, #3 and #4) of whole chicken legs (drumstick and thigh).
2. Drain packaging excess fluid from chicken part. Transfer chicken leg to sterile stomacher bags.
3. Coat samples #3 and #4 with 50 ml of 0.3% kappa carrageenan for 30 min at room temperature.
4. Squeeze fluid from chicken part and transfer coating fluid to a sterile 250 ml flask.
5. Rinse samples by adding 100 ml rinse solutions to the stomacher bags.
   #1. Butterfield's Buffer (BB)
   #2. Phosphate buffered saline with TWEEN-80 (PBST)
   #3. Phosphate buffered saline with TWEEN-80 (PBST)
   #4. 15% arginine-HCl
   Rinse chicken with a rocking motion on a shaker at 4° C. for 30 min.
6. Transfer and pool all rinse liquids from each sample into seaprate sterile 250 ml flasks. Store flask over ice to keep chilled.
7. Rinse the chicken samples again with
   #1. Butterfield's Buffer (BB)
   #2. Phosphate buffered saline with TWEEN-80 (PBST)
   #3. Phosphate buffered saline with TWEEN-80 (PBST)
   #4. Phosphate buffered saline with TWEEN-80 (PBST)
8. Adjust volume of rinse liquids to 250 ml with Butterfield's Buffer.
9. Make dilutions of $10^0$, $10^{-1}$, and $10^{-2}$.
10. Test for coliform and *E. coli* using 3M Petrifilm by transferring 1 ml of diluted samples over the gel as directed by the manufacturer.
11. Incubate gel film for 24 hr at 37° C.
12. Examine results for gas producing red (coliform) and blue colonies (confirmed *E. coli*) and blue colonies without gas (presumptive *E. coli*).

Detachment of *Salmonella* spp. from Whole Chicken Legs (Drumstick and Thigh) and Their Detection with XLT4 Agar.

Treat samples as in steps 1-8:

Non-selective Enrichment for *Salmonella*:
13. Take out 30 ml aliquot of pooled liquid wash separately into four sterile 125 ml flask.
14. Add 30 ml of double strength Buffered Peptone Water (BPW).
15. Incubate flasks at 35° C.+/−1° C. for 20-24 hr.
16. Dilute inoculum at $10^{-2}$, $10^{-3}$, $10^{-4}$ and plate 50 µl of of samples over XLT4 agar.
17. Incubate at 35° C.+/−1 for 22-24 hrs.
18. Examine for black colonies or yellow-red with black centers.

*Salmonella* spp. Detection

Results: In four trials, black colonies were not observed in all tests, indicating that *Salmonella* spp. were not detected using the non-selective enrichment broth. [These experiments were carried out in the early phase of the project and sample rinses were not enriched in RV and TT selective broths.]

Reagents: BB=Butterfield's Buffer: 0.5 mM Phosphate buffer, pH 7.2. [Ref. FDA/BAM]. PBST=Phosphate Buffered Saline with TWEEN-80 or SPAN-80: 0.5 mM Phosphate buffer, 0.9% NaCl, 0.05% TWEEN-80. INK=Carrageenan solutions are prepared aseptically by heating sterile water to 70° C. Then add the carrageenan by tapping the powder into the liquid. Break the lumps by using a sterild rod or homogenizer. Arg=15% arginine-HCl.

Summary Data on Enhanced Detachment of *E. coli* and Coliforms from Whole Chicken Legs (Drumstick and Thigh) and Their Detection with Coliform/*E. coli* Petrifilm Test.

| Sample Number | Treatment | Trial I Coliform CFU/gel | Trial I Confirmed *E. coli* CFU/gel | Trial I Presump. *E. coli* | Trial II Coliform CFU/gel | Trial II *E. coli* CFU/gel | Trial II Presump. *E. coli* |
|---|---|---|---|---|---|---|---|
| 1a | BB | 8, 5, 1 | | | 29, 1 | | |
| 1b | BB | 1, 1 | | | 15, 1 | | 1 |
| 2a | PBST | | | | 13 | | 1 |
| 2b | PBST | 1 | | | 11 | | 1 |
| 3a | INK + PBST | 60 | | | 67, 7 | 1, 1 | |
| 3b | INK + PBST | 1 | | | 77, 5, 3 | | |
| 4a | INK + Arg + PBST | 1, 1 | | | 2, 1 | 1 | 1 |
| 4b | INK + Arg + PBST | 1, 1 | | | 2, 4 | | 1 |

| Sample Number | Treatment | Trial III Coliform CFU/gel | Trial III Confirmed *E. coli* CFU | Trial III Presump. *E. coli* | Trial IV Coliform CFU/gel | Trial IV Confirmed *E. coli* CFU/gel | Trial IV Presump *E. coli*. |
|---|---|---|---|---|---|---|---|
| 1a | BB | | | | | | |
| 1b | BB | | | | | | 1 |
| 2a | PBST | | 6 | | | | |
| 2b | PBST | 1 | | 1 | | | |
| 3a | INK + PBST | | 3 | 3, 1 | 1 | | 2, 1 |
| 3b | INK + PBST | 2 | | 2 | | | 1 |
| 4a | INK + Arg + PBST | | | | | | |
| 4b | INK + Arg + PBST | | 2 | | | | |

Sample treatment, BB=Butterfield's buffer (FSIS sanctioned standard); PBST=phosphate buffer containing 0.9% sodium chloride and 0.05% TWEEN-80; INK=kappa-carrageenan; arg=arginine. Each sample was plated at three dilutions, $10^0$, $10^{-1}$, and $10^{-2}$. One ml sample was applied on Petrifilm. The manufacturer's guidelines and interpretation of results were followed. Results indicated by single numbers are detected at one dilution, typically in undiluted sample washes ($10^0$). When 2 or 3 numbers are reported, the bacteria are detected at $10^0$ and $10^{-1}$, and $10^0$, $10^{-1}$, and $10^{-2}$, respectively. The CFU reported indicate actual number per Petrifilm test and are not adjusted to sample dilution. Samples without numbers indicate that coliform or E. coli were not detected. Blank date indicate no detectable coliform or E. coli.

Figure 9A:
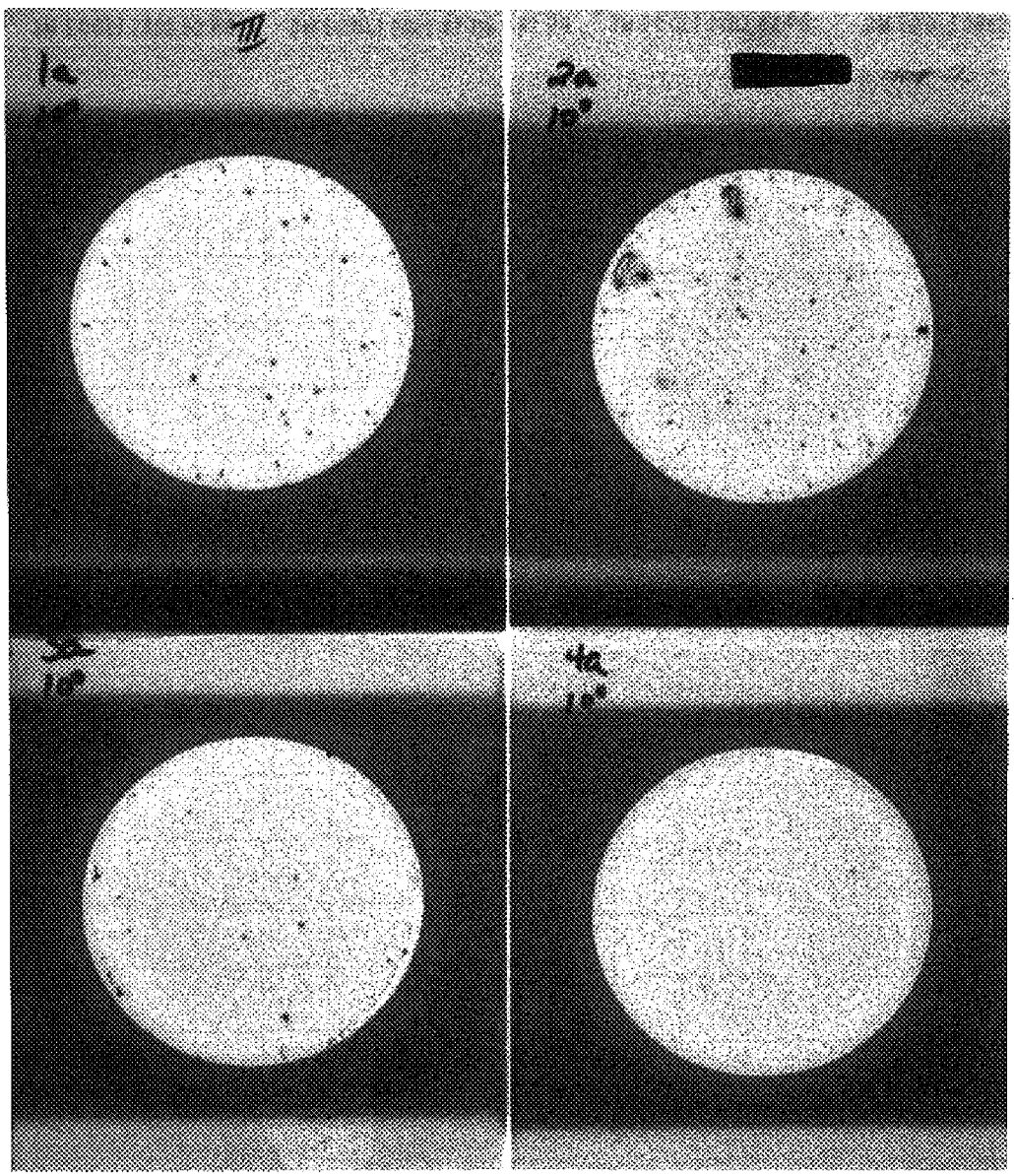
FIGS. 9A and B respectively show photos of detached coliform and and *E. coli* from the surface of chicken legs from the trials described in the table immediately before paragraph 0089 below.
Figure 9B:
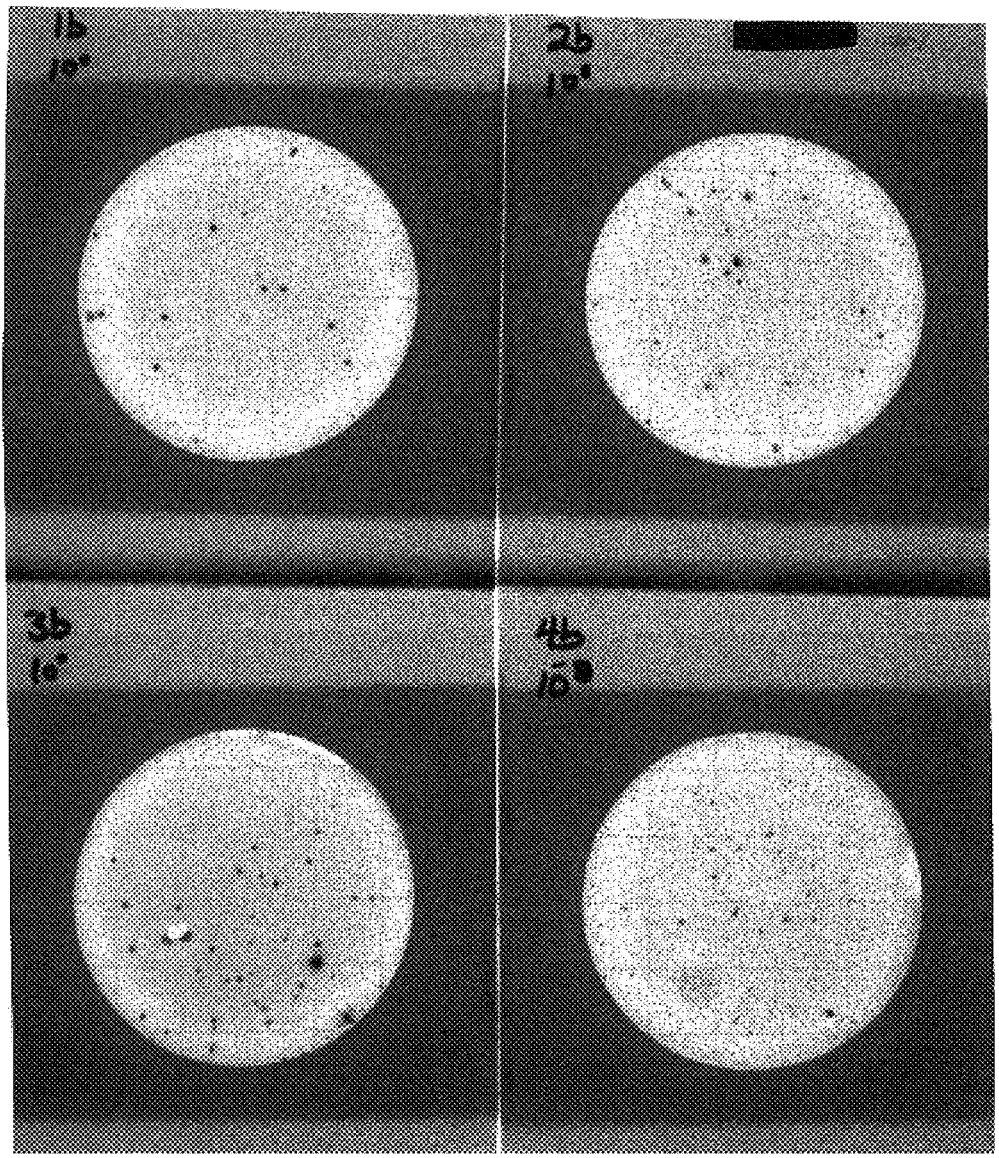

These results indicate that the treated samples (#2, 3 and 4) showed enhanced detachment of E. coli and coliform. The coliforms were indicated by red colonies with gas bubbles. Confirmed E. coli were indicated by blue to red colonies with gas bubbles while the presumptive E. coli were indicated by blue colonies without gas bubbles. In trial I, the samples had higher number of bacteria but the sample #3a treated with carrageenan and PBST detached more bacteria than with the standard Butterfield's Buffer (BB). Results of Trial III at zero dilution is shown in FIGS. 9A and B.

TABLE 1

Detachment of Collagen from E. coli 0157.H7 Sensor Surface using The Biacore Biosensor-Surface RU removed from the sensor surface by sequential treatment with guanidine and NaCl/Tween 20 or arginine and NaCl/Tween20 (numbers close to zero below (negative) suggest effective regeneration or removal of the bound ligand)

| Experiment ID | 2M guanidine | 0.75M Arginine | .25M NaCl + 0.1% Tween 20 |
|---|---|---|---|
| 990224C | 66 | | -817 |
| 990225A | -633 | | -818 |
| | 57 | | -1204 |
| | -580 | | -672 |
| | 1M Guanidine | | 25M NaCl + 0.1% Tween 20 |
| 990225B | 42 | | -112 |
| | 77 | | -16.6 |
| | -61 | | -128 |
| 990227 | | -296 | -132 |
| 990301A | | 26 | -16 |
| | | 19 | -4 |

TABLE 2

Detachment of Collagen from Salmonella Sensor Surface using The Biacore Biosensor-Surface RU removed from the sensor surface by sequential treatment with arginine and NaCl/Tween 80 (Numbers close to zero or below (negative) suggest effective regeneration or removal of the bound ligand; Tween 20 and Tween 80 regenenrated effectively the bacteria sensor surface comparde to guanidine or arginine alone; in subsequent studies, Tween 80 was used for detachment of bacteria in tissues)

| Experiment ID | 2M guanidine | 0.75M Arginine | .25M NaCl + 0.1% Tween 80 |
|---|---|---|---|
| 990227 | | 7 | -1334 |
| | | -1048 | -1385 |
| 990228 | | -44 | -63 |
| | | -95 | -97 |

TABLE 2-continued

Detachment of Collagen from Salmonella Sensor Surface using The Biacore Biosensor-Surface RU removed from the sensor surface by sequential treatment with arginine and NaCl/Tween 80 (Numbers close to zero or below (negative) suggest effective regeneration or removal of the bound ligand; Tween 20 and Tween 80 regenenrated effectively the bacteria sensor surface comparde to guanidine or arginine alone; in subsequent studies, Tween 80 was used for detachment of bacteria in tissues)

| Experiment ID | 2M guanidine | 0.75M Arginine | .25M NaCl + 0.1% Tween 80 |
|---|---|---|---|
| 990301A | | 9.4 | -24 |
| | | -41 | -68 |
| | | 18 | -3.3 |
| | | 24 | 5.1 |

TABLE 3

Detachment of E. coli 0157 in "Sandwich Immunoassay"- Surface RU removed from the sensor surface by sequential treatment with arginine and NaCl/Tween 80 (Numbers close to zero or below (negative) suggest effective regeneration or removal of the bound ligand)

| CFU | .75M Arginine | 0.25 NaCl + 0.05%Tween 80 |
|---|---|---|
| 0 | 99 | -266 |
| 10E + 3 | 237 | -29 |
| 10E + 4 | 249 | -77 |
| 10E + 5 | 275 | -100 |
| 10E + 6 | 299 | -83 |
| 10E + 7 | 405 | -234 |

TABLE 4

Detachment of Salmonella in "Sandwich Immunoassay"- Surface RU removed from the sensor surface by sequential treatment with arginin, guanidinee and NaCl/Tween 80 (Numbers close to zero or below (negative) suggest effective regeneration or removal of the bound ligand)

| CFU | .75M Arginine | 6M Guanidine | 0.25 NaCl + 0.05% Tween 80 |
|---|---|---|---|
| 0 | 75 | -137 | -534 |
| 10E + 4 | 20 | -100 | -114 |
| 10E + 5 | 32 | -54 | -42 |
| 10E + 6 | 48 | -22 | -8 |
| 10E + 7 | 96 | -32 | -18 |

All of the references cited herein are incorporated by reference in their entirety, including the following: U.S. Pat. No. 6,172,040. Medina, M. B., et al. (1997), Real-time analysis of antibody binding interactions with immobilized E. coli O157:H7, Biotechnology Techniques, Vol. 11 (3): 173-176. Medina, M. B. (1997), SPR Biosensor: Food Science Applications, Food Testing and Analysis, Vol. 3 (5), 14-15, 36. Medina, M. B. (1997), Studies on the attachment of E. coli O157:H7 on carcass components and inhibition/ detachment with food additives, 1997 ARS/FSIS Research Planning Workshop, December, Riverdale, Md., Abstract. Miller, A. J., et al. (1997), Microbial Safety Criteria for Foods Contacting Reuse Water in Food Processing Plants, 1997 Progress Report on Food Safety Research Conducted by ARS, ARS-USDA, Beltsville, Md., December 1997, pp. 80-82. Medina, M. B. (1998), Mechanisms of Enterogenic Bacterial Attachment and Inhibition of *E. coli* O157:H7 Binding to Extracellular Matrix Proteins and Tissues, Presented at the 1998 Joint PAASE, DOST and UP Conference, Manila, Philippines (Abstract and presentation). Medina, M. B. (1998), Biosensor Studies of Collagen and Laminin Binding with Immobilized *Escherichia coli* O157:H7 and Inhibition with Naturally Occurring Food Additives, Presented in SPIE's International Symposium on Industrial and Environmental Monitors and Biosensors: Pathogen Detection and Remediation for Safe Eating (EB20), Nov. 1-6, 1998, Boston, Mass. (Abstract). Medina, M. B. (1998), Biosensor Studies of Collagen and Laminin Binding with Immobilized *Escherichia coli* O157:H7 and Inhibition with Naturally Occurring Food Additives, Proceedings of SPIE—The International Society for Optical Engineering, pp. 97-104. Medina, M. B., and P. F. Fratamico, P. F. (1998), Binding interactions of collagen I, laminin and fibronectin with immobilized *E. coli* O157:H7 using surface plasmon resonance biosensor, Biotechnology Techniques, Vol. 12 (3): 235. Palumbo, S. A., and M. B. Medina. (1998), Quantitative determination of pathogen reduction during animal slaughter and food processing to provide the scientific basis of HACCP and risk assessment, 1998 Progress Report on Food Safety Research Conducted by ARS. ARS-USDA, Beltsville, Md., December 1998, pp. 90-100. Medina, M. B., et al. (1999), Scanning Electron Microscopy Studies on Attachment of *Escherichia Coli* O157:H7 to Bovine Tissues, Presented at 1999 IFT Annual Meeting, Chicago, Ill., July 24-28; Poster at Gordon Research Conference on Molecular Mechanisms of Microbial Adhesions (Aug. 1-6, 1999) and at the 18th Annual Meeting of the Philippine-American Academy of Science and Engineering, Jekyll Is., Ga., Aug. 13-15, 1999 (Abstract). Median, M. B., et al. (2001), Inhibition of *Escherichia coli* O157:H7 attachment to collagen and bovine tissues by polysulfated polysaccharides, IFT Annual Meeting and Food Expo., New Orleans, La., Jun. 23-27, 2001 (Abstract available on-line, Apr. 4, 2001). Luchansky, J. B., et al. (1999), Quantitative determination of pathogen reduction during slaughter and food processing to provide the scientific basis of HACCP and Risk Assessment, 1999 Progress Report on Food Safety Research Conducted by ARS, ARS-USDA, Beltsville, Md., December 1999, pp. 91-94.

Thus, in view of the above, the present invention concerns (in part) the following:

A method of detaching microorganisms from, or of inhibiting microbial attachment to, animal or poultry carcasses or seafood or parts thereof, said method comprising (or consisting essentially of or consisting of) contacting animal or poultry carcasses or seafood or parts thereof at least once with at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, in an amount effective to detach microorganisms from, or inhibit microbial attachment to, said animal or poultry carcasses or seafood or parts thereof.

The above method, wherein said polysulfated polysaccharide is selected from the group consisting of heparan sulfate, dextran sulfate, lambda carrageenan, kappa carrageenan, iota carrageenan, and mixtures thereof.

The above method, wherein said polysulfated polysaccharide is kappa carrageenan.

The above method, said method comprising (or consisting essentially of or consisting of) contacting animal or poultry carcasses or seafood or parts thereof at least twice with at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, in an amount effective to detach microorganisms from, or inhibit microbial attachment to, said animal or poultry carcasses or seafood or parts thereof.

The above method, said method comprising (or consisting essentially of or consisting of) contacting animal or poultry carcasses or parts thereof at least once with at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, in an amount effective to detach microorganisms from, or inhibit microbial attachment to, said animal or poultry carcasses or parts thereof.

The above method, said method comprising (or consisting essentially of or consisting of) contacting animal or poultry carcasses or parts thereof at least twice with at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, in an amount effective to detach microorganisms from, or inhibit microbial attachment to, said animal or poultry carcasses or parts thereof.

The above method, said method comprising (or consisting essentially of or consisting of) contacting animal or poultry carcasses or seafood or parts thereof at least once with at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, in an amount effective to detach microorganisms from said animal or poultry carcasses or seafood or parts thereof.

The above method, said method comprising (or consisting essentially of or consisting of) contacting animal or poultry carcasses or seafood or parts thereof at least twice with at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, in an amount effective to detach microorganisms from said animal or poultry carcasses or seafood or parts thereof.

The above method, said method comprising (or consisting essentially of or consisting of) contacting animal or poultry carcasses or parts thereof at least once with at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, in an amount effective to detach microorganisms from said animal or poultry carcasses or parts thereof.

The above method, said method comprising (or consisting essentially of or consisting of) contacting animal or poultry carcasses or seafood or parts thereof at least once with at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, in an amount effective to inhibit microbial attachment to said animal or poultry carcasses or seafood or parts thereof.

The above method, said method comprising (or consisting essentially of or consisting of) contacting animal or poultry carcasses or seafood or parts thereof at least twice with at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, in an amount effective to inhibit microbial attachment to said animal or poultry carcasses or seafood or parts thereof.

The above method, said method comprising (or consisting essentially of or consisting of) contacting animal or poultry carcasses or parts thereof at least once with at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, in an amount effective to inhibit microbial attachment to said animal or poultry carcasses or parts thereof.

The above method, wherein said non-ionic detergent is a sorbitan ester.

The above method, wherein the sorbitan ester is selected from the group consisting of polyoxyethylenesorbitan monolaurate, polyoxyethylenesorbitan monopalmitate, polyoxyethylenesorbitan monostearate, polyoxyethylenesorbitan tristearate, polyoxyethylenesorbitan monooleate, polyoxyethylenesorbitan trioleate, and mixtures thereof.

The above method, wherein the sorbitan ester is selected from the group consisting of polyoxyethylenesorbitan monolaurate, polyoxyethylenesorbitan monooleate, and mixtures thereof.

The above method, wherein the sorbitan ester is polyoxyethylenesorbitan monolaurate.

The above method, wherein the sorbitan ester is polyoxyethylenesorbitan monooleate.

The above method, wherein said non-ionic detergent is selected from the group consisting of sorbitan monolaurate, sorbitan monopalmitate, sorbitan monostearate, sorbitan tristearate, sorbitan monooleate, sorbitan trioleate, and mixtures thereof.

The above method, wherein said non-ionic detergent is selected from the group consisting of sorbitan monolaurate, sorbitan monooleate, and mixtures thereof.

The above method, wherein said non-ionic detergent is sorbitan monolaurate.

The above method, wherein said non-ionic detergent is sorbitan monooleate.

The above method, wherein said non-ionic detergent is selected from the group consisting of polyoxyethylenesorbitan monolaurate, polyoxyethylenesorbitan monopalmitate, polyoxyethylenesorbitan monostearate, polyoxyethylenesorbitan tristearate, polyoxyethylenesorbitan monooleate, polyoxyethylenesorbitan trioleate, sorbitan monolaurate, sorbitan monopalmitate, sorbitan monostearate, sorbitan tristearate, sorbitan monooleate, sorbitan trioleate, and mixtures thereof.

The above method, wherein said non-ionic detergent is selected from the group consisting of polyoxyethylenesorbitan monolaurate, polyoxyethylenesorbitan monooleate, sorbitan monolaurate, sorbitan monooleate, and mixtures thereof.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

I claim:

1. A method of detaching microorganisms from, or of inhibiting microbial attachment to, animal or poultry carcasses or seafood or parts thereof, said method consisting of contacting animal or poultry carcasses or seafood or parts thereof at least once with a solution consisting of water, at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, and optionally sodium or potassium phosphate, in an amount effective to detach microorganisms from, or inhibit microbial attachment to, said animal or poultry carcasses or seafood or parts thereof, and optionally washing said animal or poultry carcasses or seafood or parts thereof before or after said contacting.

2. The method according to claim 1, wherein said polysulfated polysaccharide is selected from the group consisting of herparan sulfate, dextran sulfate, lambda carrageenan, kappa carrageenan, iota carrageenan, and mixtures thereof.

3. The method according to claim 1, said method consisting of contacting animal or poultry carcasses or seafood or parts thereof at least twice with a solution consisting of water, at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, and optionally sodium or potassium phosphate, in an amount effective to detach microorganisms from, or inhibit microbial attachment to, said animal or poultry carcasses or seafood or parts thereof, and optionally washing said animal or poultry carcasses or seafood or parts thereof before or after said contacting.

4. The method according to claim 1, said method consisting of contacting animal or poultry carcasses or parts thereof at least once with a solution consisting of water, at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, and optionally sodium or potassium phosphate, in an amount effective to detach microorganisms from, or inhibit microbial attachment to, said animal or poultry carcasses or parts thereof, and optionally washing said animal or poultry carcasses or parts thereof before or after said contacting.

5. The method according to claim 1, said method consisting of contacting animal or poultry carcasses or seafood or parts thereof at least once with a solution consisting of water, at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, and optionally sodium or potassium phosphate, in an amount effective to detach microorganisms from said animal or poultry carcasses or seafood or parts thereof, and optionally washing said animal or poultry carcasses or seafood or parts thereof before or after said contacting.

6. The method according to claim 1, said method consisting of contacting animal or poultry carcasses or seafood or parts thereof at least once with a solution consisting of water, at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, and optionally sodium or potassium phosphate, in an amount effective to inhibit microbial attachment to said animal or poultry carcasses or seafood or parts thereof, and optionally washing said animal or poultry carcasses or seafood or parts thereof before or after said contacting.

7. The method according to claim 1, wherein said non-ionic surfactant is a sorbitan ester.

8. The method according to claim 1, wherein said non-ionic surfactant is selected from the group consisting of sorbitan monolaurate, sorbitan monopalmitate, sorbitan monostearate, sorbitan tristearate, sorbitan monooleate, sorbitan trioleate, and mixtures thereof.

9. The method according to claim 1, wherein said non-ionic surfactant is selected from the group consisting of polyoxyethylenesorbitan monolaurate, polyoxyethylenesorbitan monopalmitate, polyoxyethylenesorbitan monostearate, polyoxyethylenesorbitan tristearate, polyoxyethylenesorbitan monooleate, polyoxyethylenesorbitan trioleate, sorbitan monolaurate, sorbitan monopalmitate, sorbitan monostearate, sorbitan monooleate, sorbitan trioleate, and mixtures thereof.

10. The method according to claim 2, wherein said polysulfated polysaccharide is kappa carrageenan.

11. The method according to claim 4, said method consisting of contacting animal or poultry carcasses or parts thereof at least twice with a solution consisting of water, at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, and optionally sodium or potassium phosphate, in an amount effective to detach microorganisms from, or inhibit microbial attachment to, said animal or poultry carcasses or parts thereof, and optionally washing said animal or poultry carcasses or parts thereof before or after said contacting.

12. The method according to claim 5, said method consisting of contacting animal or poultry carcasses or seafood or parts thereof at least twice with a solution consisting of water, at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, and optionally sodium or potassium phosphate, in an amount effective to detach microorganisms from said animal or poultry carcasses or seafood or parts thereof, and optionally washing said animal or poultry carcasses or seafood or parts thereof before or after said contacting.

13. The method according to claim 5, said method consisting of contacting animal or poultry carcasses or parts thereof at least once with a solution consisting of water, at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, and optionally sodium or potassium phosphate, in an amount effective to detach microorganisms from said animal or poultry carcasses or parts thereof and optionally washing said animal or poultry carcasses or parts thereof before or after said contacting.

14. The method according to claim 1, said method consisting of contacting animal or poultry carcasses or seafood or parts thereof at least twice with a solution consisting of water, at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, and optionally sodium or potassium phosphate, in an amount effective to inhibit microbial attachment to said animal or poultry carcasses or seafood or parts thereof, and optionally washing said animal or poultry carcasses or seafood or parts thereof before or after said contacting.

15. The method according to claim 6, said method consisting of contacting animal or poultry carcasses or parts thereof at least once with a solution consisting of water, at least one member of the group consisting of (i) a polysulfated polysaccharide, (ii) carboxymethyl cellulose, (iii) guanidine or arginine, optionally together with sodium chloride and at least one non-ionic surfactant, (iv) and mixtures thereof, and optionally sodium or potassium phosphate, in an amount effective to inhibit microbial attachment to said animal or poultry carcasses or parts thereof, and optionally washing said animal or poultry carcasses or parts thereof before or after said contacting.

16. The method of claim 7, wherein the sorbitan ester is selected from the group consisting of polyoxyethylenesorbitan monolaurate, polyoxyethylenesorbitan monopalmitate, polyoxyethylenesorbitan monostearate, polyoxyethylenesorbitan tristearate, polyoxyethylenesorbitan monooleate, polyoxyethylenesorbitan trioleate, and mixtures thereof.

17. The method of claim 7, wherein the sorbitan ester is selected from the group consisting of polyoxyethylenesorbitan monolaurate, polyoxyethylenesorbitan monooleate, and mixtures thereof.

18. The method according to claim 8, wherein said non-ionic surfactant is selected from the group consisting of sorbitan monolaurate, sorbitan monooleate, and mixtures thereof.

19. The method according to claim 8, wherein said non-ionic surfactant is sorbitan monolaurate.

20. The method according to claim 8, wherein said non-ionic surfactant is sorbitan monooleate.

21. The method of claim 9, wherein said non-ionic surfactant is selected from the group consisting of polyoxyethylenesorbitan monolaurate, polyoxyethylenesorbitan monooleate, sorbitan monolaurate, sorbitan monooleate, and mixtures thereof.

22. The method of claim 16, wherein the sorbitan ester is polyoxyethylenesorbitan monolaurate.

23. The method of claim 16, wherein the sorbitan ester is polyoxyethylenesorbitan monooleate.

* * * * *